US012685874B2

(12) United States Patent
Ghiron et al.

(10) Patent No.: US 12,685,874 B2
(45) Date of Patent: Jul. 21, 2026

(54) MOTOR THRESHOLD DETECTION DEVICE FOR USE WITH A MAGNETIC STIMULATION SYSTEM

(71) Applicant: Neuronetics, Inc., Malvern, PA (US)

(72) Inventors: Kenneth Ghiron, Malvern, PA (US); Dennis Michael Sauro, Douglassville, PA (US); Daniel Zangrilli, Ardmore, PA (US); Aaron M. Kern, Phoenixville, PA (US)

(73) Assignee: Neuronetics, Inc., Malvern, PA (US)

( * ) Notice: Subject to any disclaimer, the term of this patent is extended or adjusted under 35 U.S.C. 154(b) by 513 days.

(21) Appl. No.: 18/213,673

(22) Filed: Jun. 23, 2023

(65) Prior Publication Data

US 2023/0414960 A1 Dec. 28, 2023

Related U.S. Application Data

(60) Provisional application No. 63/355,361, filed on Jun. 24, 2022.

(51) Int. Cl.
*A61N 2/02* (2006.01)
*A61B 5/11* (2006.01)
*A61N 2/00* (2006.01)

(52) U.S. Cl.
CPC ............... *A61N 2/006* (2013.01); *A61N 2/02* (2013.01)

(58) Field of Classification Search
CPC .......... A61N 2/006; A61N 2/02; A61N 2/008; A61B 5/1104; A61B 5/11; A61B 5/1101; A61B 5/1125; A61B 2560/0425

USPC ........................................... 600/13, 587, 595
See application file for complete search history.

(56) References Cited

U.S. PATENT DOCUMENTS

| | | | |
|---|---|---|---|
| 9,649,494 B2 * | 5/2017 | Gerber | ................ A61N 1/0526 |
| 2005/0107654 A1 | 5/2005 | Riehl | |
| 2013/0085316 A1 | 4/2013 | Fox et al. | |
| 2015/0190648 A1 * | 7/2015 | Fischell | ................ A61N 2/006 |
| | | | 600/14 |
| 2017/0157398 A1 | 6/2017 | Wong et al. | |
| 2017/0354831 A1 | 12/2017 | Burnett | |
| 2020/0147384 A1 | 5/2020 | Caban et al. | |

(Continued)

FOREIGN PATENT DOCUMENTS

| | | | | |
|---|---|---|---|---|
| JP | 2009512516 A | * | 3/2009 | ............... A61B 5/16 |
| JP | 2017063971 A | * | 4/2017 | |
| KR | 102312774 B1 | * | 10/2021 | ............... A61N 2/02 |

*Primary Examiner* — Brian L Casler

(74) *Attorney, Agent, or Firm* — Flaster Greenberg P.C.

(57) ABSTRACT

A system may include a plurality of depressible members, wherein each depressible member is configured to move in response to movement of one or more digits of the subject. The system may include a plurality of sensors, wherein each depressible member is associated with at least one sensor, and wherein each sensor is configured to sense movement of at least one of the plurality of depressible members. The system may receive a feedback signal from each of the plurality of sensors, receive a signal that indicates a generation time of a magnetic stimulation pulse, and determine that the feedback signal from at least one of the plurality of sensors indicates movement within a time window after the generation time of the magnetic pulse. The system may generate, via a user interface, a notification that indicates that at least one of the depressible members moved in response to the magnetic pulse.

20 Claims, 9 Drawing Sheets

(56)        References Cited

U.S. PATENT DOCUMENTS

2020/0338347 A1    10/2020  John et al.
2021/0236044 A1     8/2021  Arroyo-Gallego et al.

\* cited by examiner

MOTOR THRESHOLD DETECTION DEVICE FOR USE WITH A MAGNETIC STIMULATION SYSTEM

CROSS-REFERENCE TO RELATED APPLICATIONS

This application claims the benefit of Provisional U.S. Patent Application No. 63/355,361, filed Jun. 24, 2022, the disclosure of which is incorporated herein by reference in its entirety.

BACKGROUND

A number of medical ailments may be treated and/or diagnosed through the application of a magnetic field to an afflicted portion of a patient's body. Neurons and muscle cells may be a form of biological circuitry that carry electrical signals and respond to electromagnetic stimuli. When a conductive wire loop is passed through a magnetic field or is in the presence of a changing magnetic field, an electric current may be induced in the wire. The same principle may hold true for conductive biological tissue. When a changing magnetic field is applied to a portion of the body, neurons may be depolarized and stimulated. Muscles associated with the stimulated neurons may contract as though the neurons were firing by normal causes.

A nerve cell or neuron may be stimulated in a number of ways, for example, transcutaneously via transcranial magnetic stimulation (TMS). TMS may use a rapidly changing magnetic field to induce a current on a nerve cell, without having to cut or penetrate the skin. The nerve may "fire" when a membrane potential within the nerve rises with respect to its normal negative ambient level of approximately −90 mV, for example, depending on the type of nerve, local pH of the surrounding tissue, and/or peripheral nerve stimulation.

A magnetic stimulation component may be used to produce the rapidly changing magnetic field inducing a current on a nerve cell. The magnetic stimulation component may fail or operate improperly during treatment, which may result in improper treatment for the patient. For example, the magnetic component may appear to operate correctly, but actually may be producing magnetic field pulses outside of designed device specifications, potentially resulting in improper diagnosis and/or therapy being administered to the patient. Administering an incorrect magnetic field pulse to a patient can affect the magnetic stimulation diagnosis and/or treatment adversely. For example, the treatment provider may believe that the patient is not responding to the treatment, when in fact the intended treatment is not being administered to the patient. Thus, the treatment provider and/or diagnosing clinician may be led to make treatment decisions based on faulty information.

A typical TMS treatment apparatus may include one or more electrically conductive stimulating coils. Typical TMS treatment apparatuses generate pulsed magnetic fields that induce currents in electrically sensitive cells (e.g., nerve cells or neurons). These induced currents typically form a complete circuit in the body, such that a path of zero current through the body is created. The currents induced by a TMS treatment apparatus typically drop off to zero in approximately the middle of this path. The rate of this current drop off may be slowed, for example by spreading the current density generated the TMS apparatus over a wide surface area. However, employing this approach may concentrate return currents, which may lead to higher rates of undesirable side effects (e.g., the stimulation of untargeted regions of a subject's brain).

Prior to treatment, the user's treatment location may first be determined. For TMS, for example, the treatment location is typically determined based on the subject's motor threshold (MT) position, which itself is determined by moving the coil near a predicted area determined by patient anatomical landmarks until the desired motor response (e.g., thumb twitch) is achieved. The MT position is marked, for example, with an ink mark on the subject's head. In the case of using the TMS coil for treatment of depression, for example, the TMS therapy position is determined by moving the coil from the MT position along a line in the anterior direction a prescribed distance (e.g., a distance is 5 cm) to identify the treatment location on the subject.

For instance, current methods of determining MT position and stimulation levels for TMS studies rely on visual observation and interpretation of induced twitching of the thumb (i.e., abductor pollicis brevis) or by electromyography (EMG), which involves observation and interpretation of electrical response waveforms. In particular, a common method involves stimulating the motor cortex and observing thumb twitch or observing when the desired EMG signal exceeds a threshold value (i.e., motor evoked potential, MEP) as the stimulation level is manually adjusted. Both techniques are time consuming and highly dependent upon the skills and training of the practitioner.

SUMMARY

A method, system, and apparatus for treating or diagnosing a patient are described herein. A system is disclosed for detecting movement of one or more bodies (e.g., fingers, toes, limbs, etc.) of a human subject. The movement may be generated in response to a magnetic stimulation pulse. The system may include a motion detection device, which may include at least one (e.g., a plurality of) depressible members operably coupled to a base member. The plurality of depressible members may be configured to move about the base member in response to a movement of a respective body of the human subject. The motion detection device may include a plurality of sensors (e.g., motion sensors, such as accelerometers, tack switches actuated via movement of a spring arm, etc.). Each sensor may be coupled to a respective depressible member of the plurality of depressible members. Each sensor may be configured to detect movement of the respective depressible member.

The system may include a processor (e.g., or equivalent analog circuit comprising a comparator) that is configured to receive sensor data associated with detected movement one or more of the plurality of depressible members. The processor may be configured to receive a signal that indicates a generation time of a magnetic stimulation pulse, which for example, may be a motor threshold detection test pulse (e.g., used to locate the user's MT location and/or stimulation level). The processor may be configured to determine that the sensor data indicates movement of the one or more plurality of depressible members within a time window associated with the generation time of the magnetic stimulation pulse. Signals that are detected too soon or before the magnetic stimulation indicate that the motion is not a consequence of the stimulation. Motion after the time window may indicate a reaction to the sound of the stimulation coil being pulsed instead of a twitch caused directly by the magnetic pulse (e.g., the magnetic stimulation). The processor may be configured to generate a notification indicating that at least one of the depressible members moved in response to the magnetic stimulation pulse.

Any components of the system may include the processor. For instance, the motion detection device may include the processor. The treatment device that comprises a stimulation coil that generates the magnetic field may include the process. A user interface that includes a display device (e.g., that generates or display the notification) may include the processor. Or a component other than the motion detection device, the treatment device, and the user interface may include the processor (e.g., such as a remote server).

In some examples, the notification may indicate an amount of movement of the at least one depressible member that moved in response to the magnetic stimulation pulse. In some examples, the notification may include a meter (e.g., a bar meter) to indicate the amount of movement of the at least one depressible member that moved in response to the magnetic stimulation pulse. For instance, the meter may include first indicia that indicates the amount of movement of the depressible member during a present magnetic stimulation pulse, and/or second indicia that indicates the amount of movement of the depressible member during a previously generated magnetic stimulation pulse.

The plurality of depressible members may include a first depressible member that is configured to receive a thumb of the human subject, where for example, movement of the first depressible member indicates that a stimulation coil that generated the magnetic stimulation pulse is located at the motor threshold location of the human subject. Further, in some examples, the plurality of depressible members may also include a second depressible member that is configured to receive an index finger and a middle finger of the human subject, and/or a third depressible member that is configured to receive a ring finger and a pinky finger of the human subject.

The system may include a base that is configured to receive the subject's palm. The base may be rigidly fixed and configured to remain steady during movement by the fingers of the human subject. In some examples, the system may include a plurality of spring arms. Each of the depressible members may be associated with at least one spring arm, and the spring arm may be configured to allow the depressible member to move in response to movement of the finger of the human subject. In some examples, the system may include the user interface device, and the user interface device may include the user interface. The user interface may include a display device.

The system may include an electromagnet (e.g., a treatment coil), and a drive circuit that is electrically coupled to the electromagnet. The system may also include a second processor that is configured to control the drive circuit to provide current to the electromagnet to generate the magnetic stimulation pulse. In some examples, the second processor may be configured to provide the signal that indicates the generation time of the magnetic stimulation pulse to the processor.

A system for detecting movement of a human subject when determining a position of a motor threshold location or a treatment location of the human subject may be described herein. The system may include at least one depressible member and a processor. The depressible member may be configured to move in response to movement by the human subject. The processor may be configured to receive a feedback signal that indicates a timing of a movement of the depressible member. The processor may receive a signal that indicates a generation time of a magnetic stimulation pulse. The processor may determine that the movement of the depressible member occurred in response to the magnetic stimulation pulse. The processor may generate, via a user interface, a notification that indicates that the depressible member moved in response to the magnetic stimulation pulse.

In some examples, the system may also include a sensor that is associated with the depressible member, where the sensor is configured to sense movement of the depressible member. The system may include a treatment coil configured to generate the magnetic stimulation pulse. The system may include a display device, wherein the notification is a graphical user interface (GUI) generated via the display device. In some examples, the notification may be an audible notification (e.g., via a speaker of the treatment system). In some examples, the notification may be generated using at least one light source. The light source may be part of a motor threshold detection device. For instance, the light source may be located adjacent (e.g., right above or on) each depressible member.

The notification may indicate one or more things (e.g., to a technician of the system). For example, the notification may indicate that a treatment coil is located at the subject's motor threshold location. The notification may indicate a direction that a treatment coil should be moved so that the treatment coil is located at the subject's motor threshold location or treatment location. The notification may indicate an amount of movement of the depressible member.

A system is disclosed for detecting movement of a human subject when determining a position of a subject's motor threshold location during a treatment or diagnostic procedure (e.g., a motor threshold detection procedure, or MT procedure, that is performed during (e.g., prior to) the treatment or diagnostic procedure). The system may include a plurality of depressible members (e.g., finger paddles). Each depressible member may be configured to move in response to movement of a subject's finger. The system may include a plurality of sensors, where each depressible member is associated with at least one sensor. Each sensor may be configured to sense movement of at least one of the plurality of depressible members. The system may include a controller configured to receive a feedback signal from each of the plurality of sensors. For example, the controller may be configured to receive a signal that indicates a generation time of a magnetic stimulation pulse (e.g., a motor threshold detection test pulse). The controller may be configured to determine that the feedback signal from at least one of the plurality of sensors indicates movement above a threshold within a time window after the generation time of the magnetic stimulation pulse. The controller may be configured to generate, via a user interface, a notification that indicates that at least one of the plurality of depressible members moved in response to the magnetic stimulation pulse.

Methods and non-transitory computer-readable storage mediums for detecting movement of a human subject when determining a position of a motor threshold location or a treatment location of the human subject during a treatment or procedure may be described herein. For example, a method may include receiving a feedback signal from each of a plurality of sensors, wherein each of the plurality of sensors is associated with a depressible member of a plurality of depressible members, and where each sensor is configured to sense movement of at least one of the plurality of depressible members. The method may include receiving a signal that indicates a generation time of a magnetic stimulation pulse. The method may include determining that the feedback signal from at least one of the plurality of sensors indicates movement above a threshold within a time window after the generation time of the magnetic stimulation pulse. The method may include generating, via a user interface, a notification that indicates that at least one of the plurality of depressible members moved in response to the magnetic stimulation pulse.

DETAILED DESCRIPTION

Figure 1:
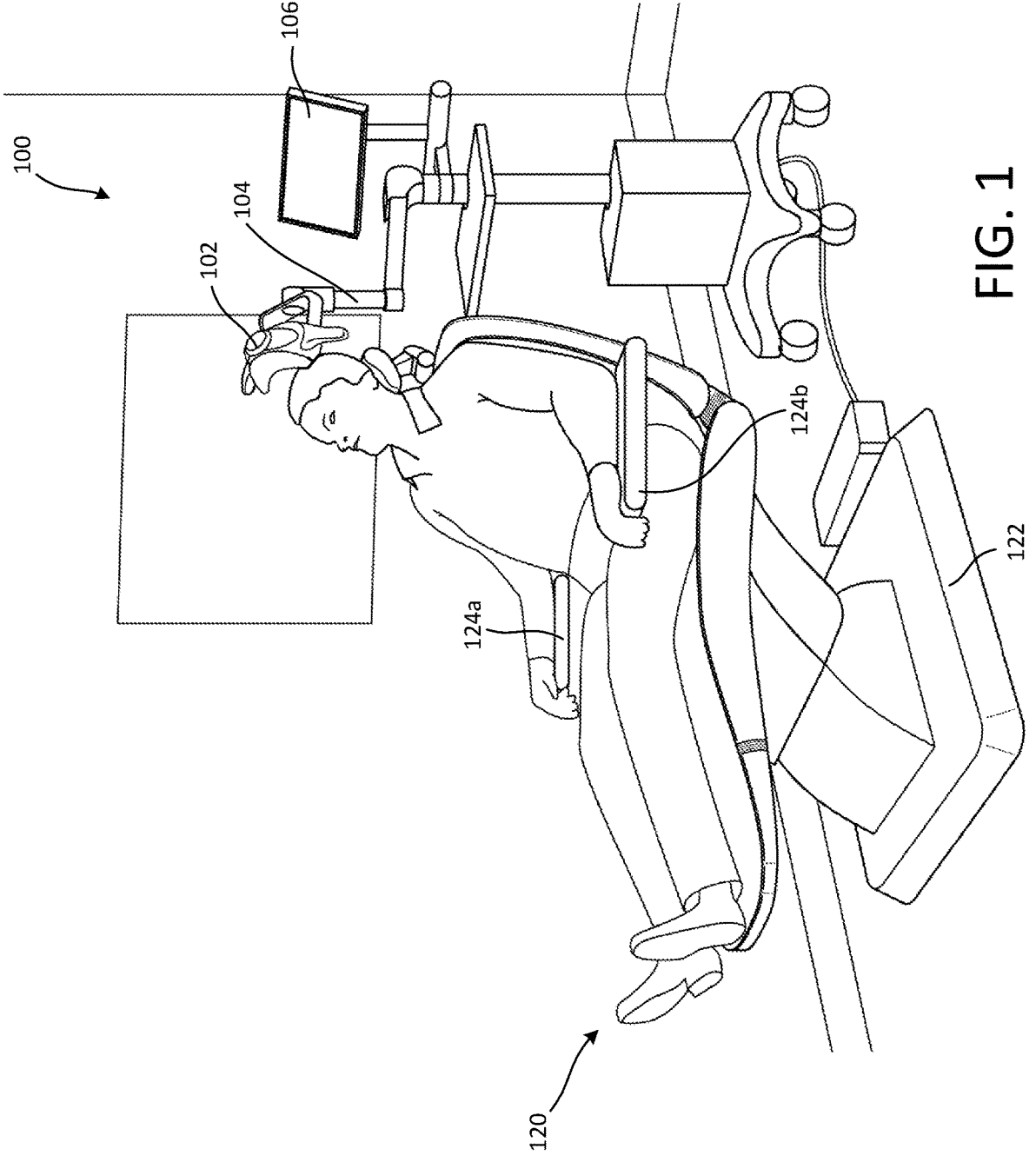
FIG. 1 is a diagram of an example of a treatment or diagnostic system.

The following discussion omits or only briefly describes conventional features of treatment or diagnostic systems, which are apparent to those skilled in the art. It is noted that various embodiments are described in detail with reference to the drawings, in which like reference numerals represent like parts and assemblies throughout the several views. Reference to various embodiments does not limit the scope of the claims attached hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

In 1831, Michael Faraday discovered that the magnitude of an electric field induced on a conductor is proportional to the rate of change of magnetic flux that cuts across the conductor. Faraday's law, well known to those skilled in the art, may be represented as $E{\sim}{-}(A{*}dB/dt)$, where E is the induced electric field in volts/meter and dB/dt is the time rate of change of magnetic flux density in Tesla/second. In other words, the amount of electric field induced in an object, such as a conductor, may be determined using two factors: the area density and the time rate of change of the flux. The greater the flux density and its derivative, the greater the induced electric field and resulting current density. Magnetic flux may be a function of distance. For example, because the magnetic flux density may decrease in strength with relation to the distance from the source of the magnetic field (e.g., $1/r^3$, $1/r^5$, or the like), the flux density may be greater closer the conductor is to the source of the magnetic field. When the conductor is a coil, the current induced in the coil by the electric field may be increased in proportion to the number of turns of the coil.

An overview of an example operation and application of a magnetic system in which aspects of the various embodiments may be implemented may be provided. The magnitude of an electric field induced on a conductor may be proportional to the rate of change of magnetic flux density across the conductor. When an electric field is induced in a conductor, the electric field may create a corresponding current flow in the conductor. The current flow may be in the same direction of the electric field vector at a given point. The peak electric field may occur when the time rate of change of the magnetic flux density is the greatest and may diminish at other times. During a magnetic pulse, the current may flow in a direction that tends to preserve the magnetic field (e.g., Lenz's Law).

Certain parts of the anatomy (e.g., nerves, tissue, muscle, brain) may act as a conductor and may carry electric current when an pulsed magnetic field is applied. The pulsed magnetic field may be applied to these parts of the anatomy transcutaneously. For example, in the context of TMS, a time-varying magnetic field may be applied across the skull to create an electric field in the brain tissue, which may produce a current. If the induced current is of sufficient density and/or duration, neuron action potential may be reduced to the extent that the membrane sodium channels open and an action potential response is created. An impulse of current may be propagated along the axon membrane that transmits information to other neurons via modulation of neurotransmitters. Such magnetic stimulation may acutely affect glucose metabolism and local blood flow in cortical tissue. In the case of major depressive disorder, neurotransmitter dysregulation and abnormal glucose metabolism in the prefrontal cortex and the connected limbic structures may be a likely pathophysiology. Repeated application of magnetic stimulation to the prefrontal cortex may produce chronic changes in neurotransmitter concentrations, metabolism, and/or nerve changes to stimulation thresholds, for example, such that depression may be alleviated.

Non-cortical neurons (e.g., cranial nerves, peripheral nerves, sensory nerves) may be stimulated by an induced electric field. For example, peripheral nerves may be intentionally stimulated to diagnose neuropathologies, for example, by observing response times and conduction velocities in response to a pulsed magnetic field induced stimulus. Discomfort and/or pain may result if the induced electric field applied to a peripheral and/or cranial nerve is very intense, and/or focused on a small area of the nerve. This discomfort may be diminished, for example, by intentionally over-stimulating the sensory nerves in the affected nerve bundle so that they can no longer respond to external pain stimuli, or by reducing the intensity and/or focus of the induced electric field that is causing the pain sensation.

Transcutaneous magnetic stimulation may not be limited to treatment of depression. Transcutaneous magnetic stimulation may be used to treat a patient, such as a human, for example, suffering from epilepsy, schizophrenia, Parkinson's disease, Tourette's syndrome, amyotrophic lateral sclerosis (ALS), multiple sclerosis (MS), Alzheimer's disease, attention deficit/hyperactivity disorder, obesity, bipolar disorder/mania, anxiety disorders (e.g., panic disorder with and without agoraphobia, social phobia also known as social anxiety disorder, acute stress disorder and/or generalized anxiety disorder), post-traumatic stress disorder (one of the anxiety disorders in DSM), obsessive compulsive disorder (e.g., one of the anxiety disorders in DSM), pain (such as, for example, migraine and trigeminal neuralgia, as well as chronic pain disorders, including neuropathic pain, e.g., pain due to diabetic neuropathy, post-herpetic neuralgia, and idiopathic pain disorders, e.g., fibromyalgia, regional myofascial pain syndromes), rehabilitation following stroke (neuro plasticity induction), tinnitus, stimulation of implanted neurons to facilitate integration, substance-related disorders (e.g., dependence, abuse and withdrawal diagnoses for alcohol, cocaine, amphetamine, caffeine, nicotine, cannabis and the like), spinal cord injury and regeneration/rehabilitation, stroke, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, autism spectrum disorders, and/or eating disorders (such as bulimia, anorexia and binge eating).

A device may take advantage of the above principles to induce an electric field used in a variety of applications. For example, a magnetic device may be used for electrical stimulation of the anatomy. While the discussion herein focuses on magnetic devices that are used in connection with magnetic stimulation of anatomical tissue, a magnetic device may be utilized in any field of endeavor. Further, as the devices provided herein are described with reference to magnetic stimulation such as, for example, Transcranial Magnetic Stimulation (TMS), the devices may be used for any treatment or diagnostic procedure (e.g., a motor threshold detection procedure, or MT procedure).

A ferromagnetic core may be used in connection with a magnetic device to produce a magnetic field. For example, a ferromagnetic core may include an arc-shaped (e.g., approximately hemispherical) magnetic material. A ferromagnetic core may include a highly saturable magnetic material having a magnetic saturation of at least 0.5 Tesla. A ferromagnetic core may be shaped to optimize the magnetic field distribution in the treatment area. For example, such a magnetic field may be for purposes of carrying out transcutaneous magnetic stimulation such as, for example, Transcranial Magnetic Stimulation (TMS), Repetitive TMS (rTMS), Magnetic Seizure Therapy (MST), deep TMS (dTMS), controlled and/or varied pulse shape TMS (cTMS), reduction of peripheral nerve discomfort, etc. Although examples described herein may be discussed in connection with TMS and rTMS, the examples described herein may be utilized in connection with any type of magnetic stimulation, such as transcutaneous magnetic stimulation, for example. Furthermore, the embodiments presented herein are not limited to the use of ferromagnetic core magnetic stimulation systems, as other core materials may be used such as, for example, an air core.

FIG. 1 is a diagram of an example of a treatment or diagnostic system 100. The treatment or diagnostic system 100 may comprise a processor (not shown), a power supply (not shown), memory (not shown), a transceiver, (not shown), a treatment coil 102 (e.g., stimulation coil), an articulating arm 104, a display device 106, a human subject positioning apparatus 122, and/or a motion detection device, such as a motor threshold detection device. One example of a motor threshold detection device is a motor threshold detection device 200 illustrated in FIG. 2A-2D. Further, in some examples, the treatment system 100 may include a user interface device that works with the motor threshold detection device, such as a motor threshold device 400 illustrated in FIG. 4A-4B. Although described as separate components, the motor threshold detection device and/or the user interface device (e.g., the function related thereto) may be incorporated into the treatment system 100.

The treatment system 100 may be stationary or movable. For example, the treatment system 100 may be integrated into a movable cart, for example, as shown in FIG. 1. In one or more examples, the treatment system 100 may be a TMS treatment system (e.g., NeuroStar®) and/or any other therapeutic and/or diagnostic procedure system.

The treatment coil 102 (e.g., an electromagnet) may be used to administer a therapeutic and/or diagnostic procedure to a human subject 120, for example, TMS. Example treatment coils 102 may include one or more treatment coils and one or more ferromagnetic components that are configured to be disposed proximate to corresponding ones of the one or more treatment coils. The one or more treatment coils and ferromagnetic components of each TMS device may cooperatively generate a magnetic field that exhibits one or more characteristics that differ from those of a magnetic field that is generated by the one or more treatment coils alone. For example, the treatment system 100 may include a drive circuit (not shown) that may be configured to cause the treatment coil 102 to generate a magnetic field. Examples of a drive circuit that may be used in the treatment system 100 are described in U.S. Pat. No. 7,744,523, which is hereby incorporated by reference in its entirety. The processor of the treatment system 100 may be configured to generate one or more drive signals (e.g., via the drive circuit) that are configured to cause the treatment coil 102 to generate a magnetic field. The magnetic field may be defined by one or more pulses in one or more pulse bursts (e.g., during a TMS treatment). The processor of the treatment system 100 may be configured to send signals to a motor threshold device (e.g., to a user interface associated with the motor threshold device) that indicate the timing and/or the power of the pulses of the magnetic field (e.g., that indicate the timing and power of the drive signals used to generate the magnetic field).

Although illustrated to include the treatment coil 102 and described primarily with respect to TMS, the treatment system 100 may include any device for administration of therapeutic and/or diagnostic procedure of the human subject. In some examples, the treatment system 100 may be used for a diagnostic procedure (e.g., solely for a diagnostic procedure). Examples of TMS coils are described in are described in U.S. Pat. Nos. 7,824,324 and 11,000,693, the contents of which are incorporated herein by reference in their entirety.

The processor (e.g., controller) of the treatment system 100 may be a general purpose processor, a special purpose processor, a conventional processor, a digital signal processor (DSP), a plurality of microprocessors, one or more microprocessors in association with a DSP core, a microcontroller, Application Specific Integrated Circuits (ASICs), Field Programmable Gate Array (FPGAs) circuits, any other type of integrated circuit (IC), a state machine, and the like. The processor may perform signal coding, data processing, power control, input/output processing, and/or any other functionality that enables the treatment system 100 to operate. The processor may be integrated together with one or more other components of the treatment system 100 in an electronic package or chip.

The processor of the treatment system 100 may be coupled to and may receive user input data from and/or output user input data to the treatment coil 102, the articulating arm 104, the display device 106 (e.g., a liquid crystal display (LCD) display unit or organic light-emitting diode (OLED) display unit), and/or the human subject positioning apparatus 122. The processor may access information from, and store data in, any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The processor may access information from, and store data in, memory that is not physically located within the treatment system 100, such as on a server (not shown).

The memory may comprise a computer-readable storage media or machine-readable storage media that maintains computer-executable instructions for performing one or more as described herein. For example, the memory may comprise computer-executable instructions or machine-readable instructions that include one or more portions of the procedures described herein. The processor of the treatment system 100 may access the instructions from memory for being executed to cause the processor to operate as described herein. The memory may comprise computer-executable instructions for executing configuration software. For example, the computer-executable instructions may be executed to perform, in part and/or in their entirety, one or more procedures as described herein. Further, the memory may have stored thereon one or more settings and/or control parameters associated with the treatment system 100, a motor threshold detection device, and/or the user interface for a motor threshold detection device.

The processor may receive power from the power supply, and may be configured to distribute and/or control the power to the other components in the treatment system 100. The power supply may be any suitable device for powering the treatment system 100.

The human subject 120 may be positioned within the human subject positioning apparatus 122. The human subject positioning apparatus 122 may be a chair, recliner, bed, stool, and/or the like. When performing treatment, the treatment coil 102 may be situated such that the human subject's head is positioned under the treatment coil 102. The treatment coil 102 may be adjusted by means of the articulating arm 104 and/or the like. The human subject positioning apparatus 122 may include one or more arms, such as a right arm 124a and a left arm 124b as shown in FIG. 1. Although not illustrated in FIG. 1 and as described in more detail below, the right and/or left arm 124a, 124b of the human subject positioning apparatus 122 may include a motor threshold detection device (e.g., the motor threshold detection device 200 of FIG. 2A). The motor threshold detection device may be permanently or removable mounted to the right arm 124a and/or the left arm 124b of the human subject positioning apparatus 122. The motor threshold detection device may be connected to the processor of the treatment system 100, for example, via an electrical connection and/or a wireless connection. In some examples, the motor threshold detection device may include a dedicated display device (not shown), while in other examples, the motor threshold detection device may use the display device 106 of the treatment system 100.

The motor threshold detection device may include one or more movement detection sensors, such as accelerometers, to detect movement of one or more body parts of the human subject 120, such as, but not limited to, fingers, a foot, or the like. The treatment system 100 (e.g., the motor threshold detection device) may be configured to detect movement of the human subject's 120 fingers that is a result from a magnetic pulse generated by the treatment coil 102. For instance, the treatment system 100 may use the motor threshold detection device to detect movement of the fingers of the human subject 120 within a certain time period after a pulse is generated (e.g., movement that occurs within 0.25 second after the generation of the magnetic pulse). The treatment system 100 may ignore movements outside of the time period. It is noted that the examples provided herein correspond to the motor threshold detection device of the treatment system 100 detecting movement of one or more fingers of the human subject 120. However, it should be understood that the motor threshold detection device may detect other bodily movements of the human subject 120 (e.g., a foot of the human subject 120), and examples of detecting bodily movement of the human subject 120 are not limited to only detecting movement of one or more fingers of the human subject 120 (e.g., when treating other disorders, such as OCD or PTSD).

The treatment system 100 may comprise one or more computer software applications stored in memory of the treatment system and/or running on the processor. The computer software applications may provide a system graphical user interface (GUI) (e.g., a TMS system GUI) on the display device 106. The computer software applications may incorporate work flow management to guide a technician through the therapeutic and/or diagnostic procedure, and/or supervise and/or control one or more subsystems of the treatment system 100. For example, the computer software applications may control internal system functions, monitor the system status to ensure safe operation, and/or provide the user with a graphical means to manage the preparation for and/or the administration of the therapeutic and/or diagnostic procedure.

Interaction with the computer software applications may be provided via a user interface. In one or more embodiments, the user interface device may be the display device 106, which may be a touch screen display. The display device 106 may include touch activated images of alphanumeric keys and/or buttons for user interaction with the treatment system 100. The display device 106 may provide graphic representations of the system activity, messages, and/or alarms. Interactive buttons, fields, and/or images may be displayed via the display device 106, and may enable the technician to direct and/or interact with system functions, for example, such as entering data, starting and stopping the procedure, running diagnostics, adjusting positioning and/or configuration of the treatment coil 102, adjusting the position of one or more sensor(s), and/or the like.

The treatment system 100 may be used for any therapeutic and/or diagnostic procedure. For example, the treatment system may be used for TMS, transcranial direct current stimulation (tDCS), Electroencephalography (EEG), Deep brain stimulation (DBS), a diagnostic procedure, and/or the like. For example, the treatment system 100 may be used for any therapeutic and/or diagnostic procedure that includes the placement of electrodes, sensors, probes, and/or the like on a human subject, such as on the surface of a human subject's head. Although described with reference to a head model, the treatment system 100 may be configured to generate a model of any part of the human subject 120, such as, but not limited to, the arm, neck, chest, leg, foot, and/or the like. Example methods of using the treatment system 100 to determine the human subject's 120 MT location and/or treatment location are described in U.S. Pat. Nos. 7,104,947 and 9,884,200, the contents of which are incorporated herein by reference in their entirety.

Further, as noted above, prior to treatment, the treatment location of the human subject 120 may first be determined. For TMS, for example, the treatment location is typically determined based on the subject's MT position, which itself is determined by moving the coil near a predicted area determined by patient anatomical landmarks until the desired motor response (e.g., thumb twitch) is achieved. This process may be referred to as a motor threshold detection procedure, and may be part of the TMS treatment procedure (e.g., may be a preliminary step that is performed prior to generating one or more treatment pulse burst sets). In addition to detecting the location of the MT position, the treatment system 100 may also be used to detect the power of the pulses needed to cause the neurons at the MT location to be depolarized and stimulated (e.g., until the desired motor response in the human subject 120 (e.g., thumb twitch) is achieved). As described in more detail herein, the treatment system 100 may determine the human subject's 120 MT position and power level using the motor threshold detection device.

After the location of the MT position and the power level of a test pulse is detected, the MT position and power level may be stored. For example, the MT position may be marked, for example, with an ink mark on the subject's head, or the MT position may be stored within the processor of the treatment system. Further, the power level of the test pulse may be stored, for example, in the memory of the treatment system 100. The treatment location may then be determined using the MT position. For example, in the case of using the TMS coil for treatment of depression, the TMS treatment location is determined by moving the coil from the MT position along a line in the anterior direction a prescribed distance (e.g., a distance is 5 cm) to identify the treatment location on the human subject 120.

Figures 2A, 2B:
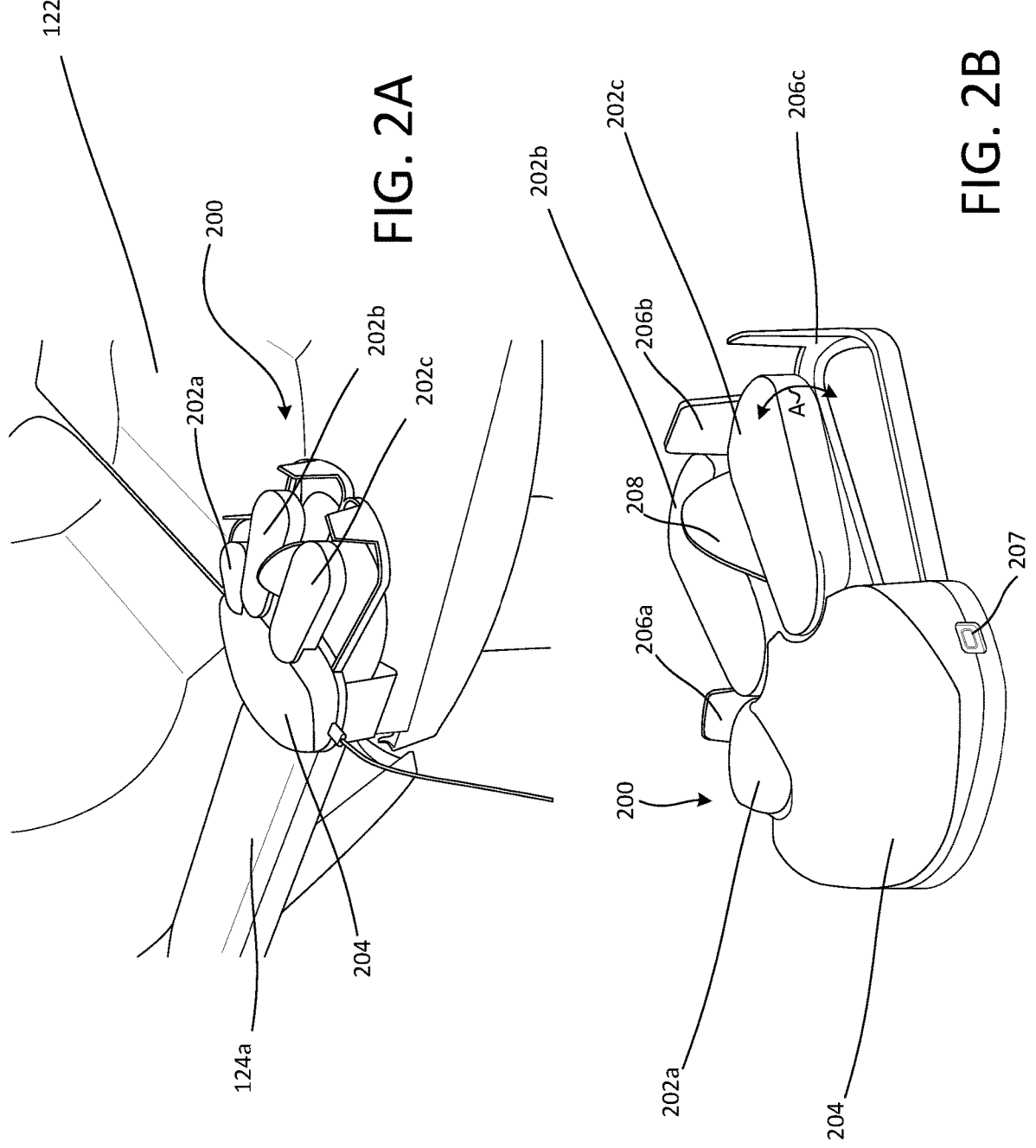
FIG. 2A is a perspective view of an example motor threshold detection device mounted to a human subject positioning apparatus.
FIG. 2B is a perspective view of an example motor threshold detection device not mounted to a human subject positioning apparatus.

FIG. 2A is a perspective view of an example motor threshold detection device 200 mounted to a human subject positioning apparatus (e.g., the human subject positioning apparatus 122). FIG. 2B is a perspective view of the motor threshold detection device 200 not mounted to a human subject positioning apparatus. As described herein, the motor threshold detection device 200 may be configured to be fixable attached or removable attached to a human subject positioning apparatus. For instance, in some examples, the motor threshold detection device 200 may be provided separately from any treatment system (e.g., treatment system 100), and may be attached to or used alongside an existing treatment system.

The motor threshold detection device 200 may be configured to detect the movement of one or more fingers (e.g., or other body parts) of a human subject. For example, the motor threshold detection device 200 may include one or more depressible members operably coupled to a base 204. For example, the motor threshold detection device 200 device may include three depressible members 202a, 202b, 202c, as shown in FIGS. 2A and 2B. However, in other examples, the motor threshold device may include more or less than three depressible members. In some examples, the depressible member(s) may be finger paddles. The depressible member(s) may have a rigid surface configured to interface with a body (e.g., one or more fingers) of a human subject (e.g., the human subject 120). For example, the surface of the depressible member may have an ergonomic shape configured to interface with a body (e.g., one or more fingers) of the human subject. In some examples, the surface of the depressible member has a planar surface. The depressible member may be a finger paddle configured to move in response to a movement of the human subject's finger.

The base 204 includes a fixed rigid surface sized to accommodate a palm of the human subject. In some cases, the surface of the base 204 has an ergonomic shape configured to interface with the body (e.g., a palm) of the human subject. In other cases, the surface of the base 204 may have a planar surface. In some examples, the base 204 and depressible members 202a-c may be arranged with respect to one another in an ergonomic configuration such that the human subject may comfortably rest a portion of the body (e.g., palm, thumb, and index, middle, ring, and little fingers) on the motor threshold detection device 200.

A removeable hygiene barrier (not shown) may be placed on the surface of the depressible members 202a, 202b, 202c and the base 204 before proceeding with a procedure, such as example procedure 800. The hygiene barrier may be removed from the surface of the depressible members 202a, 202b, 202c and the base 204 after the completion of the procedure. In some examples, the hygiene barrier may include a 3-Layer construction that includes a non-woven fabric liner, an adhesive layer configured to contact and temporarily adhere to a surface, and a release liner configured to protect the adhesive layer before use of the hygiene barrier. The hygiene barrier may include a tab having a non-adhesive area that allows for the easy release from the release liner as well as repositioning and/or removal after use.

The depressible members may be sized to accommodate any number of bodies of the human subject. For example, the depressible members 202a, 202b, and 202c may be positioned around the base 204, such that the depressible member 202a may be sized to interface with a thumb (i.e., digit 1) of the human subject, the depressible member 202b may be sized to interface with the index and middle fingers (i.e., digits 2 and 3) of the human subject, and the depressible member 202c may be sized to interface with the ring and little fingers (i.e., digits 4 and 5) of the human subject. In another example, the motor threshold detection device 200 may include five depressible members, such that each depressible member is sized to interface with a respective finger of the human subject. In yet another example, the motor threshold detection device 200 may include two depressible members, such that a depressible member may be sized to interface with a thumb (i.e., digit 1) of the human subject and another depressible member may be sized to interface with the index, middle, ring, and little fingers of the human subject.

The motor threshold detection device 200 may include a communication port 207, which may interface with a printed circuit board (PCB) (e.g., PCB 224) of the motor threshold detection device 200. The communication port 207 may enable electronic communication between the motor threshold detection device 200 and a controller (e.g., processor) of the treatment system (e.g., the treatment system 100). For instance, as described more herein, the communication port 207 may allow the motor threshold detection device 200 to send one or more signals to a motor threshold detection device user interface and/or to the treatment system that indicate an amount and/or a timing of an actuation of each depressible member 202a-c.

Figure 2C:
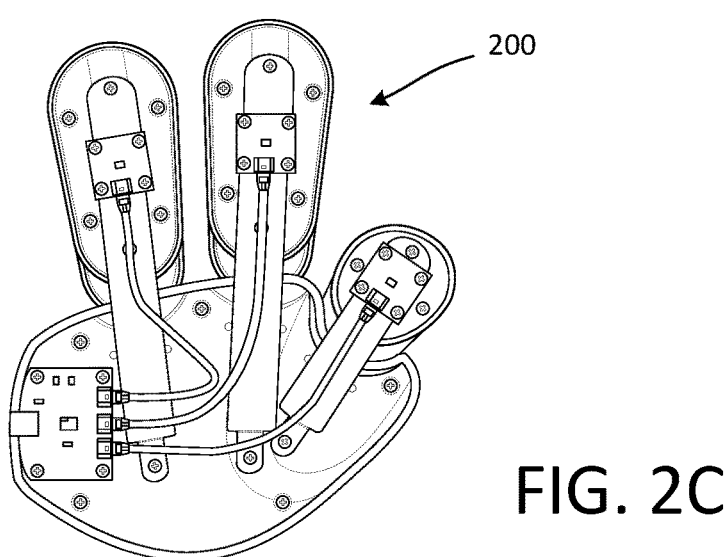
FIG. 2C is a cross-sectional bottom view of the example motor threshold detection device of FIGS. 2A and 2B.
Figure 2D:
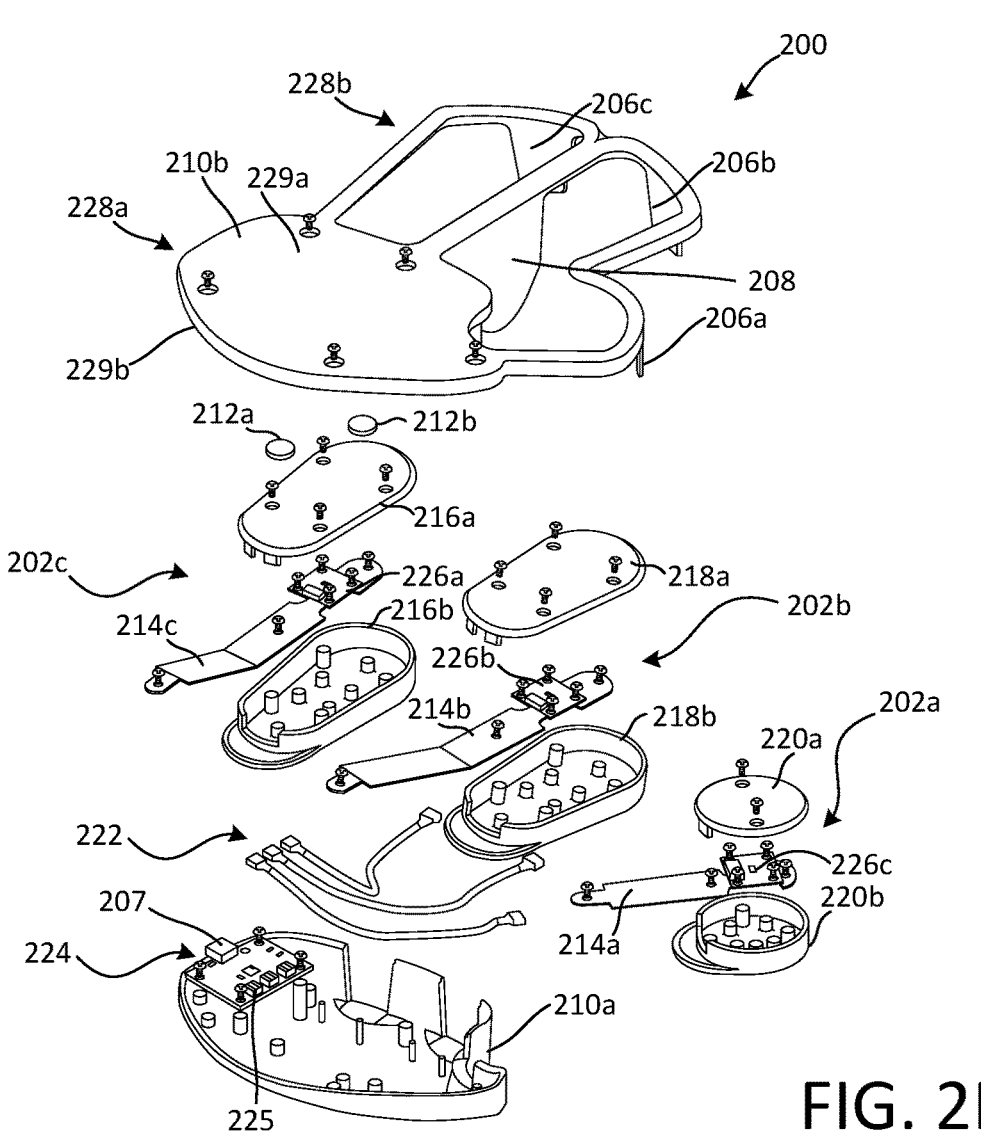
FIG. 2D is an exploded view of the example motor threshold detection device of FIGS. 2A, 2B, and 2C.

FIG. 2C is a cross-sectional bottom view of the example motor threshold detection device 200 of FIGS. 2A and 2B. FIG. 2D is an exploded view of the example motor threshold detection device 200 of FIGS. 2A, 2B, and 2C. The base 204 of the motor threshold detection device 200 may include a top housing 210a coupled with a bottom housing 210b. The top housing 210a may include the surface that interfaces with a palm of the human subject. The top housing 210a may be shaped to house one or more electronic components of motor threshold detection device 200. For example, the top housing 210a may house a printed circuit board (PCB) 224, portions of cables 222, and/or portions of spring arms 214a, 214b, and 214c. The PCB 224 may include one or more communication ports 207 for one or more connectors, such as a connector to the processor of a treatment system (e.g., the treatment system 100) and/or a connector to a motor threshold detection device user interface.

The bottom housing 210b may include a first portion 228a that couples to the top housing 210a. The bottom housing 210b may include a second portion 228b that extends from a proximal end of the first portion 228a to a distal end of the second portion 228b, such that the second portion 228b extends beyond the top housing 210a. For example, the second portion 228b of the bottom housing 210b may extend from the proximal end of the first portion 228a to the distal end of the second portion 228b, such that the second portion 228b encompasses an area of one or more of the depressible members, such as depressible members 202a, 202b, and 202c.

In some examples, the distal end of the second portion 228b may include guards, such as guards 206a, 206b, and 206c that protrudes upwards from the bottom housing 210b. The guards 206a, 206b, and 206c may be rigid member protruding upwards from the inner surface 229b of the bottom housing 210b. The guards 206a, 206b, and 206c may be configured to prevent an object from contacting one or more of the depressible members 202a, 202b, and 202c and/or bodies (e.g., fingers) positioned on the depressible members 202a, 202b, and 202c during a procedure, such as the example procedure 800 described herein. In some examples, the bottom housing 210b may include a guard per depressible member, where for example, the guard is positioned adjacent (e.g., in front) of the depressible member. For example, the guard 206a may be positioned in front of depressible member 202a, the guard 206b may be positioned in front of depressible member 202b, and the guard 206c may be positioned in front of depressible member 202c.

The bottom housing 210b may include one or more dividing members, such as dividing member 208, that protrude upwards from the bottom housing 210b. The dividing member 208 may be a rigid protrusion that extends upwards from the inner surface 229b of the bottom housing 210b and in between two depressible members, such as depressible members 202b and 202c. The dividing member 208 may be configured to separate two bodies of the human subject positioned on the two depressible members, such as depressible members 202b and 202c. For example, dividing member 208 may separate index and middle fingers (i.e., digits 2 and 3) of the human subject that are positioned on depressible member 202b from the ring and little fingers (i.e., digits 4 and 5) of the human subject that are positioned on the depressible member 202c. The dividing member 208 may be provided to prevent bodies (e.g., the index and middle fingers) positioned on one depressible member (e.g., depressible member 202b) from inadvertently contacting another depressible member (e.g., depressible member 202c).

The bottom housing 210b includes a dividing member 208 between depressible members 202b and 202c, and does not include a dividing member 208 between depressible member 202a and 202b. However, examples are contemplated in which the bottom housing 210b includes a dividing member 208 between each depressible member 202a, 202b, and 202c. Yet, other cases are contemplated in which the bottom housing 210b includes a dividing member 208 between adjacent depressible members but not between other adjacent depressible members. Further, other cases are contemplated in which the bottom housing 210b does not include any dividing members 208.

A depressible member may include a top housing coupled with a bottom housing, such that a sensor and a portion of a spring arm reside within the top housing and bottom housing. For example, the depressible member 202a may include a top housing 220b and a bottom housing 220a that are coupled with one another. The top housing 220b and the bottom housing 220a may house a sensor 226c and a distal end portion of a spring arm 214a. Further, the depressible member 202b may include a top housing 218b and a bottom housing 218a that are coupled with one another. The top and bottom housing 218a, 218b may house a sensor 226b and a distal end portion of spring arm 214b. The depressible member 202c may include a top housing 216b and a bottom housing 216a that are coupled with one another. The top and bottom housing 216a, 216b may house a sensor 226a and a distal end portion of spring arm 214c.

The sensors 226a, 226b, and 226c may be fastened to the distal end portions of the respective spring arms, such as spring arm 214a, 214b, and 214c. Each sensor may be configured to detect movement of a respective depressible member via the respective spring arm. For example, the sensor 226a may be configured to detect movement of depressible member 202c when the spring arm 214c moves in direction A, as illustrated in FIG. 2B. For instance, if either or both of the ring and little fingers (i.e., digits 4 and 5) of the human subject move (e.g., twitch) the depressible member 202c, the sensor 226a may detect that the depressible member 202c moved, and thus indicate that either or both of the ring and little fingers also moved. Similarly, the sensor 226b may be configured to detect movement of depressible member 202b when the spring arm 214b moves in direction A, as illustrated in FIG. 2B. And the sensor 226c may be configured to detect movement of depressible member 202a when the spring arm 214a moves in direction A, as illustrated in FIG. 2B.

The sensors 226a, 226b, and 226c may be operably coupled and provide information to the PCB 224 via cables 222. For example, as described more herein, the sensors 226a, 226b, and 226c may send one or more signals to the PCB 224 that indicate an amount and/or a timing of an actuation of each, respective depressible member 202a-c. The PCB 224 may comprise a processor 225 that is configured to receive the signals from each respective sensor 226a, 226b, and 226c. In some examples, the signals may be voltage signals that indicate the timing and/or the amount of actuation for each respective sensor 226a, 226b, and 226c. The processor 225 may be configured to process the signals, and provide signals via the communication port 207 to the user interface device and/or a treatment system that indicate the amount and/or the timing of an actuation of each, respective depressible member 202a-c. As such, a user interface device and/or a treatment system may be configured to receive the signals that indicate the amount and/or the timing of an actuation of each, respective depressible member 202a-c.

The sensors 226a, 226b, and 226c may comprise accelerometers or any other sensors capable of detecting motion of an object. In some examples, a proximal end portion of the spring arm is fastened to the base 204 and a distal end portion of the spring arm is fastened to the respective depressible member. The distal end portion of the spring arm may be fastened to the respective depressible member, such that the distal end portion of the spring arm and the respective depressible member are fixed to one another and move in unison as an object (e.g., an index finger) contacts and moves the depressible member. Alternatively or additionally, in some examples, the sensors 226a, 226b, and 226c may comprise a passive infrared (PIR) sensor, an ultrasonic sensor, a tack switch that is configured to be actuated via movement of a spring arm 214a, 214b, and 214c, and/or the like.

The motor threshold detection device 200 may be fixed to an object, such as an arm of a human subject positioning apparatus (e.g., the right arm 124a or the left arm 124b of the human subject positioning apparatus 122), via the first portion 228a of the bottom housing 210a. For example, the first portion 228a includes one or more magnets (e.g., neodymium magnets), such as magnets 212a and 212b, positioned on an inner surface 229b of the first portion 228a and configured to magnetically couple to the object.

Figure 3:
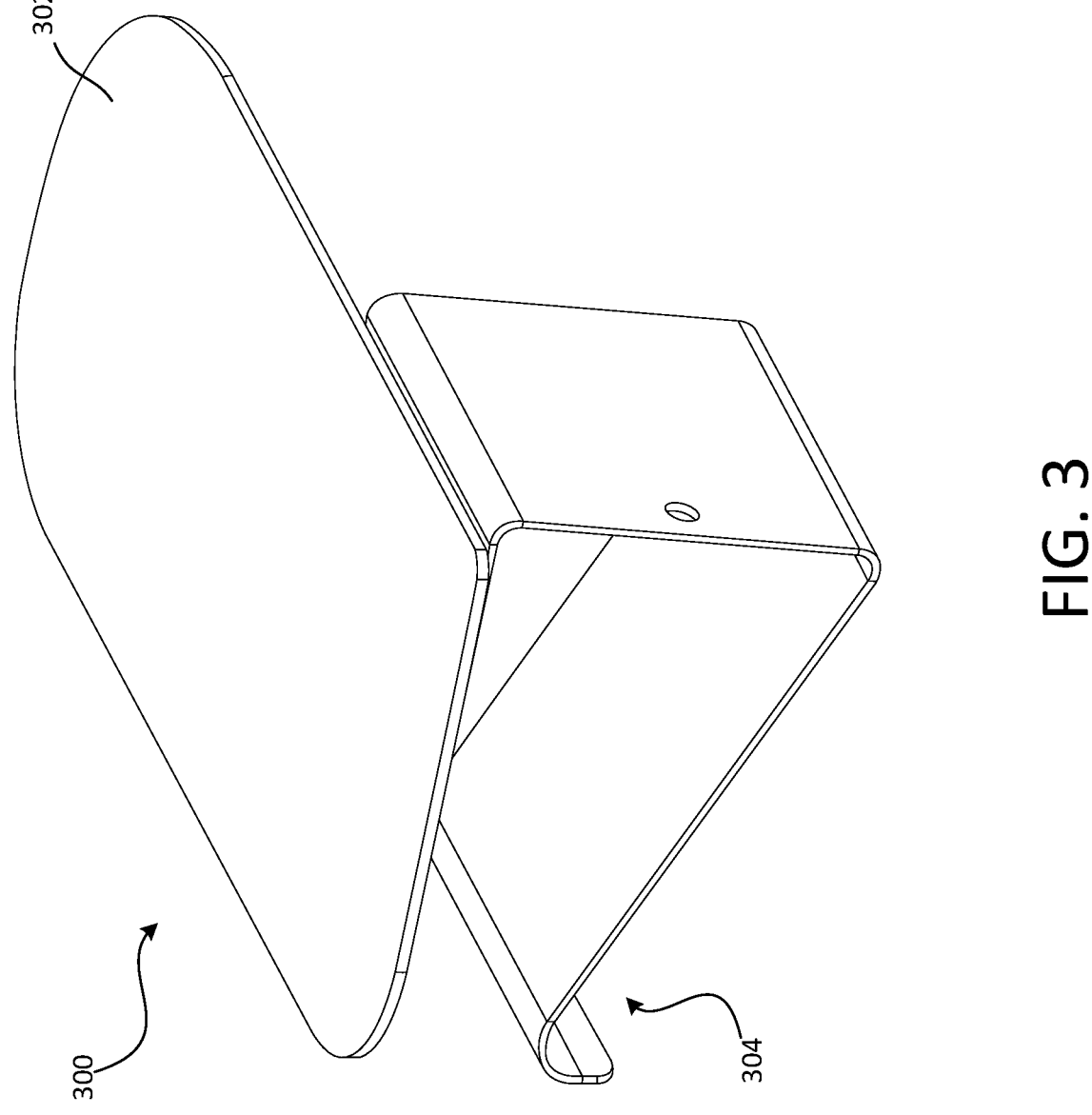
FIG. 3 is a perspective view of an example arm rest base to support a motor threshold detection device.

FIG. 3 is a perspective view of an example arm rest base to support a motor threshold detection device (e.g., the motor threshold detection device 200). The treatment system (e.g., the treatment system 100) may include the arm rest base 300. The arm rest base 300 may include a planar surface 302 coupled with an attachment member 304. In some examples, an outer surface 229a of the first portion 228a of the bottom housing 210a may rest on the planar surface 302 of the arm rest base 300.

The planar surface 302 of the arm rest base 300 may be formed from a metal material capable of magnetically coupling to the first portion 228a of the bottom housing 210a via the one or more magnets, such as magnets 212a and 212b. Although two magnets 212a, 212b are illustrated, the motor threshold detection device 200 may include more or less magnetics. By magnetically coupling the motor threshold detection device 200 to the planar surface 302 of the arm rest base 300, the motor threshold detection device 200 may be easily positioned for the best fit and comfort of the human subject. In some examples, the attachment member 304 may be shaped to fit around and couple to a portion of an object, such as an arm of a human subject positioning apparatus (e.g., the right arm 124a or the left arm 124b of the human subject positioning apparatus 122). The shape of the attachment member 304 may provide a clamping force, such that when the attachment member 304 is expanded outwards to fit around, for instance, the arm of the human subject positioning apparatus, the attachment member 304 may utilize the clamping force to couple to the arm. As such, the spring-like design of the attachment member 304 may allow for easy attachment to and removal from the arm of the human subject positioning apparatus. Moreover, the spring-like design of the attachment member 304 may allow for the arm rest base 300 and the motor threshold detection device to be easily positioned along a length of the arm of the human subject positioning apparatus into a preferred position to provide the best fit and comfort for the human subject.

It is noted that the arm rest base 300 may be coupled to an object, such as the arm of the human subject positioning apparatus, via other means, such as via adhesives, fasteners, clamps, and the like, and is not limited to coupling to an object via only the attachment member 304. Moreover, it should be understood that the motor threshold detection device 200 may be fixed or removable coupled to a stationary object via other means (e.g., adhesive or Velcro removably coupling a bottom surface 229a of the motor threshold detection device 200 to a surface of the arm of a human positioning apparatus) and without the use of the arm rest base 300.

Figures 4A, 4B:
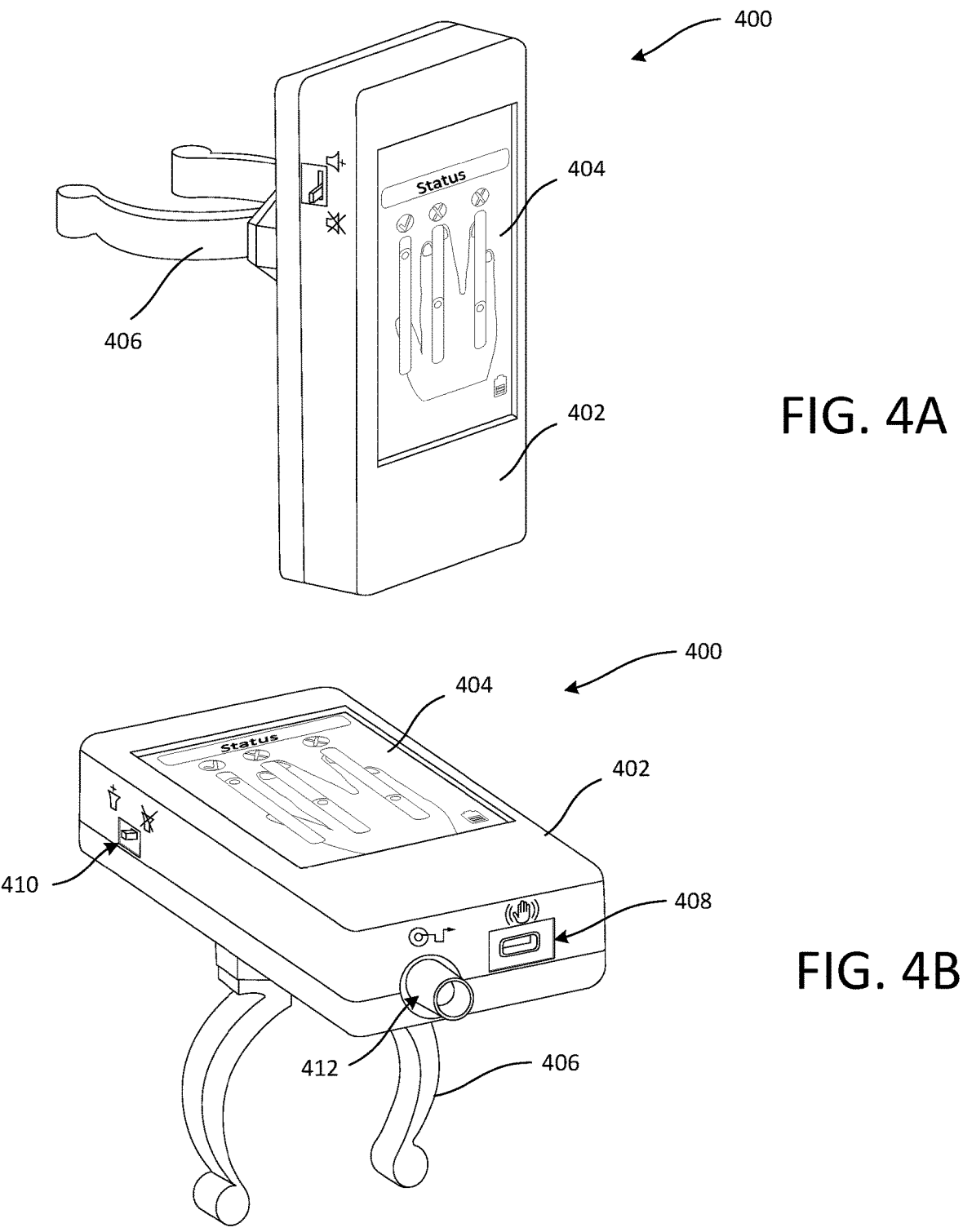
FIG. 4A is a front perspective view of a user interface device that may be dedicated to a motor threshold detection device.
FIG. 4B is a bottom perspective view of the user interface device of FIG. 4A.

FIG. 4A is a front perspective view of a user interface device 400 that may be used along with a motor threshold detection device (e.g., the motor threshold detection device 200). FIG. 4B is a bottom perspective view of the user interface device 400. The motor threshold detection device may be used along with a treatment system (e.g., the treatment system 100). The user interface device 400 may include a housing 402. The user interface device 400 may include a display device 404, a power on/off button (not shown), a motor threshold detection device port 408, a volume button 410, and/or a system port 412.

The motor threshold detection device port 408 may be operatively coupled to a motor threshold detection device (e.g., the motor threshold detection device 200). As such, the corresponding signals of the motor threshold detection device (e.g., those signals generated by the processor of the motor threshold detection device 200 in response to the signals provided by sensors 226a, 226b, and 226c) may be received by the user interface device 400. In response, the user interface device 400 may present information via the display device 404 that indicates the amount and/or the timing of an actuation of each, respective depressible member of the motor threshold detection device.

The system port 412 may be coupled to a treatment system. The system port 412 may be configured to receive signals (e.g., timing signals) from the treatment system that indicate the timing of a pulse of a magnetic field generated by the treatment coil of the treatment device. In some examples, the signal received from the treatment system may be a drive signal that is used by the treatment system to generate the magnetic field. For instance, in some examples, the signal received from the treatment system may be a square wave signal where the rising edges of the square wave indicate the start time of each pulse and the falling edges indicate the end time of each pulse. Alternatively, in some examples, the signal received from the treatment system may be a digital signal. As such, the user interface device 400 may be configured to determine the timing between the pulse of the magnetic field generated by the treatment coil and the actuation of a depressible member of the motor threshold detection device. As such, using the motor threshold detection device port 408 and the system port 412, the user interface device 400 may receive signals from the motor threshold detection device that indicate the amount and/or the timing of an actuation of each, respective depressible member, and at the same time receive signals (e.g., timing signals) from the treatment system that indicate the timing of the pulses of the magnetic field generated by the treatment coil of the treatment device.

Further, in some examples, the user interface device 400 may be configured to receive power from the treatment device via the system port 412. Further, the user interface device 400 may include an internal power supply (not shown) that is located within the housing 402 to power the components of the user interface device 400.

The user interface device 400 may include a processor (not shown) and memory (not shown) that resides within the housing 402 of the user interface device 400. The processor may be configured to receive the signals from the motor threshold detection device that indicate the amount and/or the timing of an actuation of each, respective depressible member. The process may be configured to receive signals (e.g., timing signals) from the treatment system that indicate the timing of the pulses of the magnetic field generated by the treatment coil of the treatment device (e.g., the timing of test pulses used to determine a MT location prior to treatment). The processor may store these signals in memory and/or may generate one or more user interfaces (UIs) for display on the display device 404.

The processor of the user interface device 400 may be configured to determine whether the movement of a depressible member of the motor threshold detection device occurred in response to (e.g., coincides with) a pulse of the magnetic field generated by the treatment coil of the treatment device (e.g., a motor threshold detection pulse). The processor may be configured to generate a UI that indicates whether movement a depressible member of the motor threshold detection device occurred in response to (e.g., coincides with) a pulse of the magnetic field generated by the treatment coil of the treatment device. As such, the technician using the user interface device 400 may receive a clear indication of whether movement of a user's finger that caused a depressible member to move occurred in response to a pulse of the magnetic field or whether it was just an unrelated movement by the human subject (e.g., a false positive). Therefore, the user interface device 400 can differentiate between movements caused by the magnetic field and movements that are unrelated to the magnetic field (e.g., a false positive). Further, although described as being performed by the processor of the user interface device 400, in other examples, the processor of the treatment system and/or the processor of the motor threshold detection device may be configured to receive the respective signals from the motor threshold detection device and the treatment system, and determine whether the movement of a depressible member of the motor threshold detection device occurred in response to a pulse of the magnetic field generated by the treatment coil of the treatment device (e.g., or was a false positive).

The user interface device 400 may provide feedback to a user, such as a technician, that indicates the amount and/or the timing of an actuation of each, respective depressible member of a motor threshold detection device that occurred, and also provide confirmation that the actuation of the depressible member resulted from a pulse of the magnetic field generated by the treatment device. For example, the processor may be configured to generate a UI on the display device that indicates (e.g., illustrates) whether the motor threshold detection device detects movement of each depressible member(s). For instance, the processor may be configured to generate a UI on the display device that indicates whether the motor threshold detection device detects movement of a depressible member associated with the patient's thumb, which may be indicative of the coil be at the patient's motor threshold (MT) location. Accordingly, the processor may be configured to generate a UI on the display device 404 that indicates information that indicates whether a TMS coil is orientated over the MT location and/or whether the TMS coil is pulsed at a level that is sufficient to cause neurons at the MT location to be depolarized and stimulated.

The user interface device 400 may include a mounting clip 406, such that the user interface device 400 may be mounted in fixed position for a user to view. For example, during the example procedure 800, the technician may mount the user interface device 400 to an articulating arm of the treatment system (e.g., the articulating arm 104). It is noted that the user interface device 400 may be provided in the treatment system, as provided feedback (e.g., those signals provided by the sensors 226a, 226b, and 226c) may be displayed on a display device of treatment system (e.g., the display device 106).

Further, in some examples, the user interface device 400 may be configured to perform one or more tests to ensure that the motor threshold detection device and/or the treatment system are connected correctly and/or working property, for example, based on signals received via the motor threshold detection device port 408 and/or the system port 412. For example, the user interface device 400 (e.g., and/or the treatment system) may be configured to enter a mode (e.g., a demonstration mode) where, when in that mode, the treatment system may generate a trigger signal that simulates a magnetic pulse and/or the motor threshold detection device may be configured to generate a signal that stimulates the movement of one or more depressible members. The user interface device 400 may receive the signal from the trigger signal that simulates a magnetic pulse and determine whether the connection between the user interface device and the treatment system is working properly. The user interface device 400 may receive the signal that stimulates the movement of one or more depressible members and determine whether the sensors of the motor threshold detection device are working properly. The user interface device 400 may run either test on a periodic basis.

In some examples, the treatment system (e.g., the processor of the treatment system) may receive the output signal of the motor threshold detection device that indicates the amount and/or timing of the movement of a depressible member of the motor threshold detection device. The treatment system may receive the signal in addition to or as an alternative to the user interface device 400 receiving the output signal of the motor threshold detection device. In such examples, the treatment system may be configured to automatically adjust the level (e.g., power level) of a subsequent pulse of a magnetic field generated by the treatment coil based on the output signal of the motor threshold detection device that indicates the amount and/or timing of the movement of a depressible member of the motor threshold detection device. For example, if the output signal indicates that a depressible member associated with the thumb of the user moved, but only moved slightly, then the treatment system may increase the power of a subsequent pulse of the treatment coil, for example, in an effort to increase the movement of the thumb of the patient (e.g., to exceed a threshold associated with a sufficient MT level for treatment, such as TMS).

Further, in some examples, the treatment system (e.g., the treatment system 100) may include a robotic arm that is configured to move the treatment coil relative to the patient (e.g., relative to the patient's head). For instance, the processor of the treatment system may be configured to control the movement of the treatment coil prior to, or during, a MT processor or the treatment procedure itself. An example of robotic arm for a TMS coil is described in U.S. Pat. No. 8,845,508, which is incorporated herein by reference in its entirety. In examples where the treatment system comprises a robotic arm, the treatment system may be configured to automatically adjust the position of the treatment coil prior to the generation of a subsequent pulse of the magnetic field based on the output signal of the motor threshold detection device that indicates the amount and/or timing of the movement of a depressible member of the motor threshold detection device that occurred in response to a prior pulse of a magnetic field. For example, if the output signal indicates that the patient's middle and/or ring finger moved in response to a prior magnetic pulse, the treatment system may be configured to cause the robotic arm to move the treatment coil in a direction closer to the patient's MT location and pulse the coil again, for example, with the hopes that the subsequent pulse cases the patient's thumb to twitch. As such, using the motor threshold detection device and a robotic arm, the treatment system may be configured to automatically adjust the position of the treatment coil and search for the user's MT location using the output signal(s) received from the motor threshold detection device, for example, without requiring the technician to physically move the treatment coil relative to the patient's head.

In some examples, the user interface device 400 may be integrated into a treatment system (e.g., the treatment system 100), for example, such that the system includes a treatment system and a motor threshold detection device. In such instances, the output of the motor threshold detection device may be received by the treatment system (e.g., the processor of the treatment system), and the treatment system may be configured to determine whether the movement of a depressible member of the motor threshold detection device occurred in response to (e.g., coincides with) a pulse of the magnetic field generated by the treatment coil of the treatment device (e.g., a motor threshold detection pulse). Further, the processor of the treatment system may be configured to provide feedback to the technician that indicates the amount and/or the timing of an actuation of each, respective depressible member of a motor threshold detection device that occurred, and/or provide confirmation that the actuation of the depressible member resulted from a pulse of the magnetic field generated by the treatment device. In such instances, the user interface device 400 may be omitted because, for example, the functionality of the user interface device 400 may be performed by the treatment system.

Figures 5A, 5B, 5C:
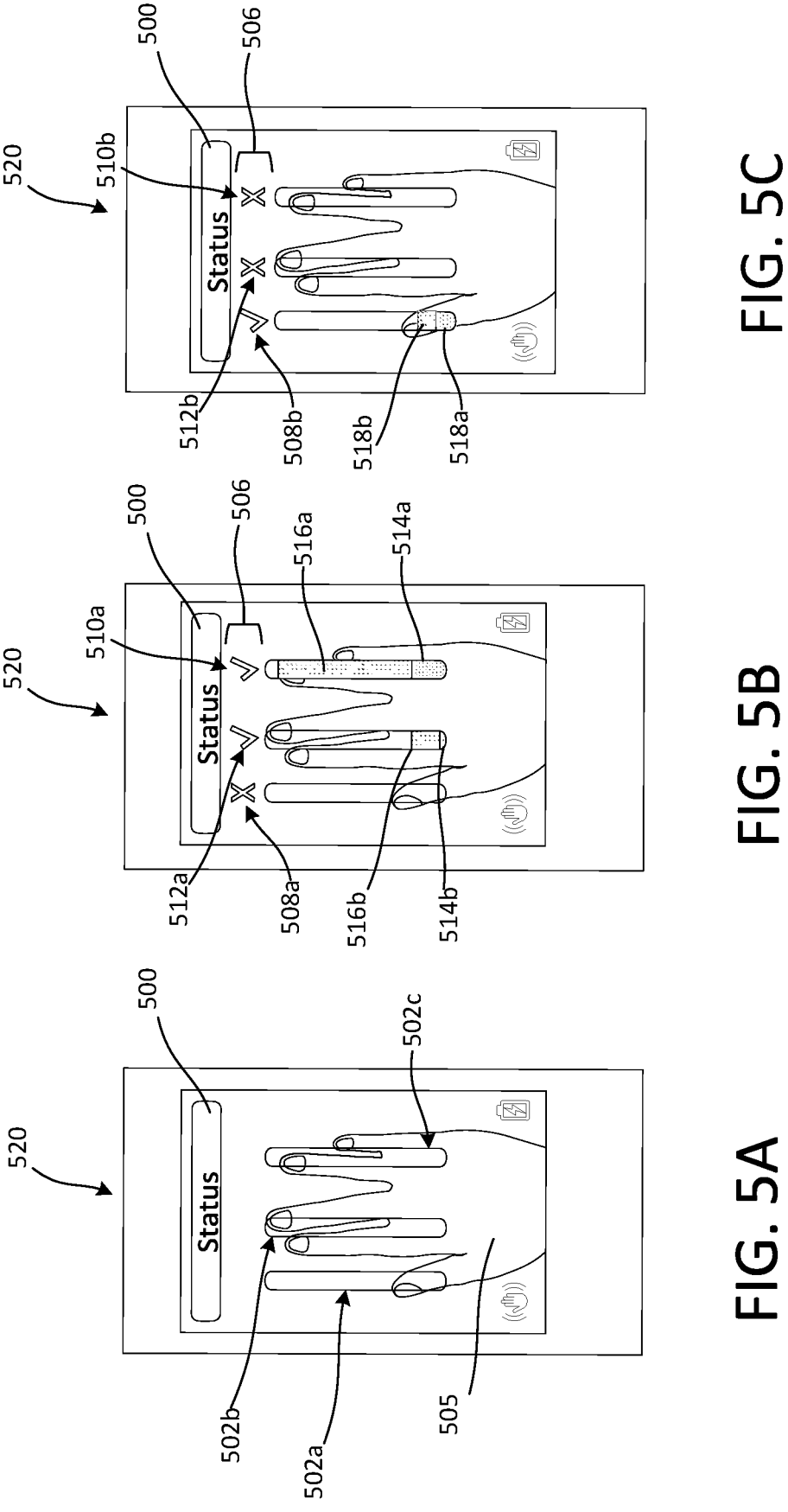
FIG. 5A is a perspective view of the example user interface device of FIG. 4A prior to a treatment system generating a motor threshold pulse.
FIG. 5B is a perspective view of the example user interface device of FIG. 4A after the treatment system generates a motor threshold pulse and the motor threshold detection device detects movement of two example depressible members.
FIG. 5C is a perspective view of the example user interface device of FIG. 4A after the treatment system of generates a motor threshold pulse and the motor threshold detection device detects movement of one example depressible member.

FIG. 5A is a perspective view of a display device 520 prior to a treatment system (e.g., the treatment system 100) generating a motor threshold pulse. FIG. 5B is a perspective view of the display device 520 after the treatment system generates a motor threshold pulse and a motor threshold detection device (e.g., the motor threshold detection device 200) detects movement of two depressible members (e.g., the depressible members 202b, 202c). FIG. 5C is a perspective view of the display device 520 after the treatment system generates a motor threshold pulse and the motor threshold detection device detects movement of one depressible member (e.g., the depressible member 202a). The display device 520 may be an example of the display device 404 of the user interface device 400 and/or the display device 106 of the treatment system 100. Accordingly, the processor of the user interface device 400 and/or of the treatment system 100 may be configured to control the display device 520 to generate the UIs portrayed in FIGS. 5A-5C.

The display device 520 may generate a UI that includes one or more of a status indicator 500, a plurality of meters, such as bar meters. Although described in context of bar meters, the display device 520 may be configured to generate a UI that include meters of other types (e.g., line charts, etc.) that provide a status of the amount and/or timing of feedback relating to detected motion of the depressible members of the motor threshold detection device. The illustrated example provides a first bar meter 502a, a second bar meter 502b, and a third bar meter 502c, and a movement indicator 506. The status indicator 500 may provide a status of the motor threshold detection device during an MT procedure, such as the example the procedure 800. For instance, the status indicator 500 may display an indication that the motor threshold detection device is waiting for a timing signal (e.g., a synchronization signal) of a magnetic pulse from the treatment system. Having detected a timing signal, the status indicator 500 may display an indication that the received data is being processed. Further, in some examples, the status indicator 500 may also display instructions to a user (e.g., technician) of the treatment system as to the current or next steps to perform the MT procedure. In some examples, the status indicator 500 may display an indication of whether the presence of the patient's hand is detected by the motor threshold detection device (e.g., in instances where the motor threshold detection device includes a sensor that is configured to detect whether the human subject's hand is touching the depressible members).

The plurality of bar meters may provide feedback relating to detected motion of the depressible members of the motor threshold detection device. For instance, referring to the motor threshold detection device 200, the first bar meter 502a may provide feedback for the depressible member 202a, the second bar meter 502b may provide feedback for the second depressible member 202b, and the third bar meter 502c may provide feedback for the third depressible member 202c.

The plurality of bar meters may be overlayed on a reference image 505 displayed on the display device 520. The reference image 505 may be used as a guide to detect movements of the respective body parts of the human subject that are positioned on the respective depressible members of the motor threshold detection device. For example, the reference image 505 may be an image of a hand, in which the first bar meter 502a is overlayed on a thumb (i.e., digit 1) of the hand, the second bar meter 502b is overlayed on the index and middle fingers (i.e., digits 2 and 3) of the hand, and the third bar meter 502c is overlayed on the ring and little fingers (i.e., digits 4 and 5) of the hand.

As noted herein, the display device 520 may be an example of the display device 404 of the user interface device 400 and/or the display device 106 of the treatment system 100. And the user interface device may be coupled to the motor threshold detection device (e.g., via the motor threshold detection device port 408) and the processor of the user interface device may be configured to receive signals from the motor threshold detection device that indicate the amount and/or the timing of an actuation of each, respective depressible member of the motor threshold detection device. Further, at the same time, the user interface device may be configured to receive a signal (e.g., a timing signal) from the treatment device (e.g., via the system port 412) that indicates the timing of a pulse of a magnetic field generated by the treatment coil of the treatment device. As such, the user interface device may be configured to determine whether the movement of a depressible member of the motor threshold detection device occurred in response to a pulse of the magnetic field generated by the treatment coil of the treatment device (e.g., or was a false positive), and in response, generate a GUI that indicates, via indicia, that a depressible member was moved in response to a pulse of the magnetic field.

The movement indicator 506 may provide an indicium of a detected movement of a respective depressible member. For example, when a movement of a depressible member (e.g., the depressible member 202a, 202b, or 202c) is detected, the display device 520 may display a positive indicium (e.g., a check mark 508b, 510a, or 512a) of the respective depressible member. Further, when a movement of a depressible member (e.g., a depressible member 202a, 202b, or 202c) is not detected, the display device 520 may display a negative indicium (e.g., an "X" 508a, 510b, 512b) of the respective depressible member in which movement was not detected.

In some examples, each bar meter 502a, 502b, 502c may provide feedback relating to the amount of movement of a respective depressible member of the connected motor threshold detection device. For example, the display device 520 may illuminate a greater amount of the bar meter in response to detecting a greater amount of movement of the respective depressible member. As such, the display device 520 may provide feedback which illustrates a strength or amount of movement of the human subject (e.g., a strength or movement of a finger twitch). The processor of the user interface device or treatment system that includes the display device 520 may determine an amount to illuminate a bar meter based on the received signals provided by the respective sensors of the motor threshold detection device (e.g., sensors 226a, 226b, 226c). For example, the processor of the user interface device or treatment system may determine that the accelerometer data provided by sensor 226c indicates a large movement of the depressible member 202c and the accelerometer data provided by sensor 226b indicates a small movement of the depressible member 202b. As such, the display device 520 may illuminate an area 514a of bar meter 502c and illuminate an area 514b of bar meter 502b, in which the illuminated area 514a is greater than the illuminated area 514b. In some examples, the illuminated areas may be displayed in a variety of indicators (e.g., colors, textures, and the like). Further, in some examples, the display device 520 may display the illuminated areas generated in response to a magnetic pulse with a consistent indicator, such that illuminated areas generated in response to one magnetic pulse may be distinguishable from illuminated areas generated in response to another magnetic pulse.

The display device 520 may display detected movements of one or more magnetic pulses from the treatment system. For instance, referring to FIG. 5B, the processor may detect movement of depressible members 202b and 202c during a time window around a signal received from the treatment system that indicates that a first magnetic pulse was generated. In some examples, the time window may be 250 ms after the magnetic pulse was generated. In other examples, the time window may be set such that it is between 20 ms to 250 ms after the magnetic pulse was generated. In response, the processor may cause the display device 520 to illuminate areas 514a and 514b of the bar meters 502b and 502c, respectively. Prior to generating a second magnetic pulse, a technician may move the position of a treatment coil on the human subject, for example, to locate the MT location (e.g., the location that will result in a magnetic pulse causing the human subject's thumb to twitch, resulting in movement of the depressible member 202a). Alternatively or additionally, the technician may increase the power (e.g., strength) of the magnetic field.

Still referring to FIG. 5B, the processor of the user interface device may receive data from the motor threshold detection device 200 indicating movement of the depressible members 202b and 202c during the time window around a signal received from the treatment system that indicates that a second magnetic pulse was generated. In response, the processor may cause the display device 520 to illuminate areas 516a and 516b of the bar meters 502b and 502c, respectively. Further, to assist the technician, the display device 520 may include both the illuminated areas 516a and 516b that indicate the movement of the depressible members 202b and 202c that occurred in response to the second magnetic pulse, as well as the illuminated areas 514a and 514b that indicate the movement of the depressible members 202b and 202c that occurred in response to a prior magnetic pulse. As such, the technician may infer that the power level of the second magnetic pulse was greater than the first magnetic pulse (e.g., and/or that the treatment coil was moved toward the MT location) because the movement of the depressible members 202b and 202c increased in response to the generation of the second magnetic pulse. However, since the user interface device did not detect movement of the depressible member 202a, the processor is configured to not illuminate the bar meter 502a, which indicates that the treatment coil is not located over the MT location of the human subject.

Referring to FIG. 5C, the technician may again move the position of the treatment coil on the human subject and cause the treatment system to generate a subsequent magnetic pulse. As such, the motor threshold detection device may generate a signal that indicates movement of the depressible member 202a during the time window around a signal received from the treatment system that indicates that the subsequent magnetic pulse was generated. In response, the processor of the user interface device may cause the display device 520 to illuminate area 518a of the bar meter 502a. In some cases, the technician may generate a series of magnetic pulses without repositioning the treatment coil on the human subject. In doing so, the technician may confirm the position of the treatment coil on the human subject. For instance, the technician may generate a subsequent magnetic pulse at the same location, but at a higher power level. The motor threshold detection device may generate a signal that again indicates movement of depressible member 202a, and the processor of the user interface device may cause the display device 520 to illuminate area 518b of the bar meter 502a. The area 518b may be larger than the area 518a because the subsequent magnetic pulse was generated at a higher power level, which resulted in a more significant motor response (e.g., a larger thumb twitch) of the human subject.

Figure 7B:
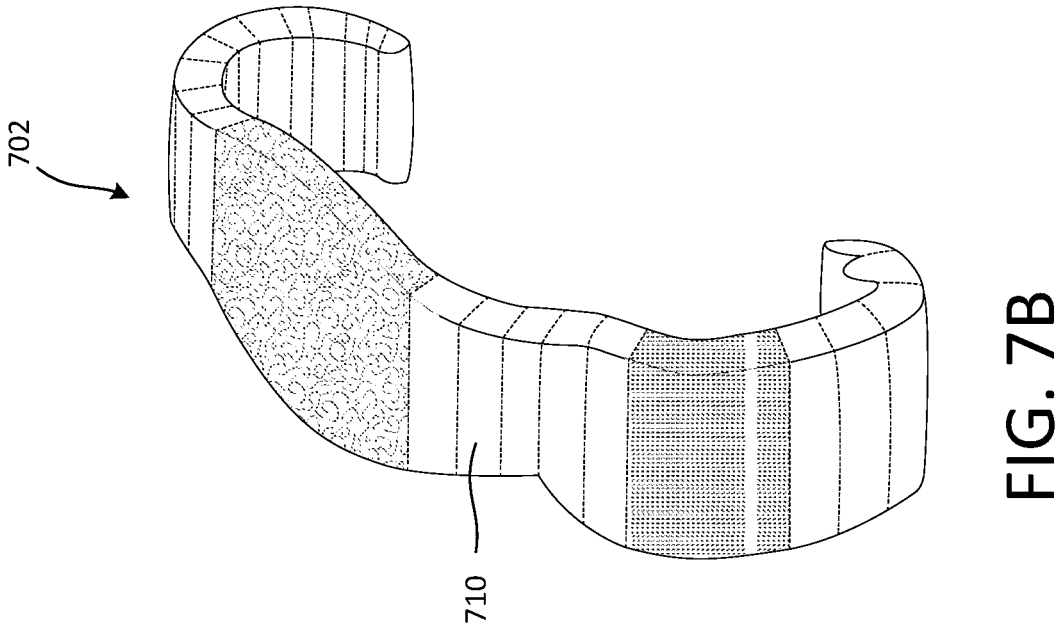
FIG. 7B is an example diagram of the central sulcus and the primary motor cortex of the human brain of FIG. 7A.
Figure 7A:
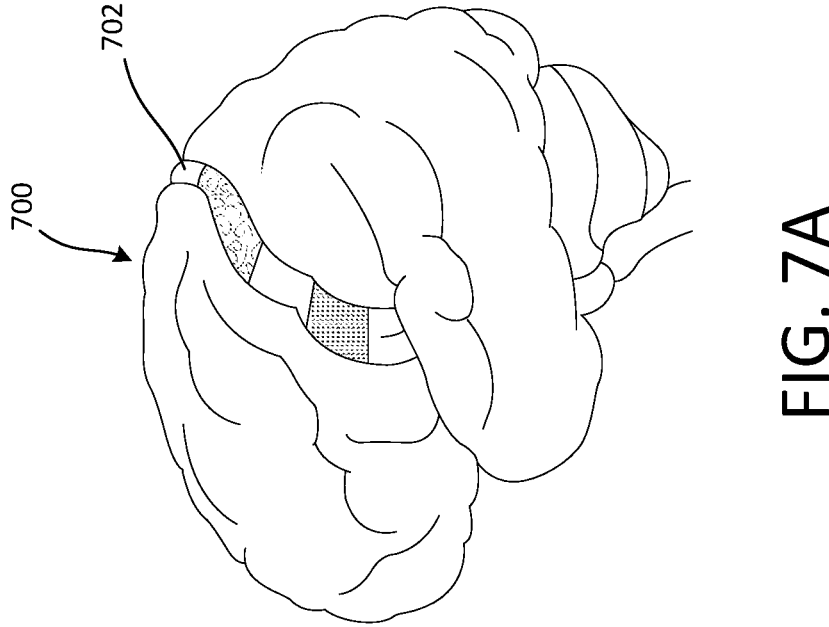
FIG. 7A is an example of the human brain.

By illuminating areas of respective bar meters and displaying the illuminated areas associated with detected movements of depressible members from different magnetic pulses, the technician may be assisted when attempting to position the treatment coil on the human subject and navigate various areas of the brain of the human subject. For instance, the technician may use the illuminated areas to navigate a central sulcus 702 the cerebral cortex of a brain 700 of the human subject (e.g., the human subject 120), as illustrated in FIGS. 7A and 7B, to identify a particular position on the central sulcus 702, such as an area 710 that controls the movement of the subject's thumb, which may be the MT location for treatment of particular disorders (e.g., such as depression). Further, although the feedback from just a single prior pulse is illustrated in FIGS. 5B and 5C (e.g., the illuminated area 514a and 514b in FIG. 5B, and the illuminated area 518a of FIG. 5C), in some examples, the display device 520 may be configured to display feedback that indicates the detected movements of depressible members that occurred in response to a plurality of prior magnetic pulses.

Figure 6:
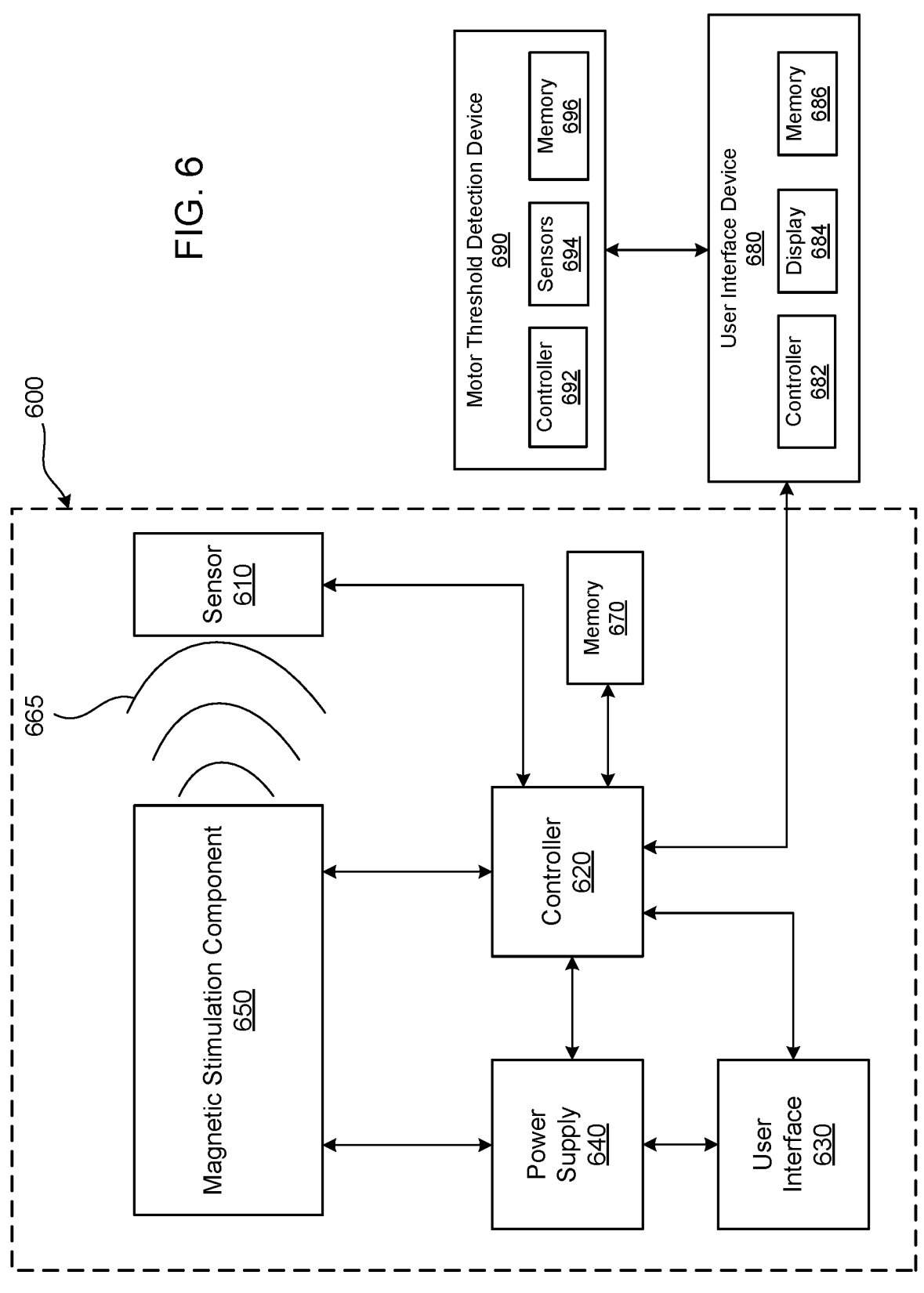
FIG. 6 is a block diagram illustrating an example of a magnetic stimulation system.

FIG. 6 is a block diagram illustrating an example of a magnetic stimulation system 600. The magnetic stimulation system 600 may be an example of the treatment system 100. The magnetic stimulation system 600 may comprise a sensor 610, a controller 620, a user interface device 630, a power supply 640, and a magnetic stimulation component 650. The magnetic stimulation component 650 may be an example of the treatment coil 102 of the treatment system 100 of FIG. 1.

The magnetic stimulation component 650 may be configured to generate a pulsing magnetic field 665 to conduct magnetic stimulation therapy on a treatment area of a patient, such as the human subject 120. The magnetic stimulation therapy may be, for example, transcranial magnetic stimulation (TMS). TMS may refer to TMS, repetitive transcranial magnetic stimulation (rTMS), deep TMS (dTMS), cTMS, or the like. The magnetic stimulation component 650 may be a treatment coil. The magnetic stimulation component 650 may include a single treatment coil, multiple treatment coils, and/or an array of treatment coils. The treatment area may be, for example, but not limited to a location within the brain 700 that is determined using the area 710 that controls the movement of the subject's thumb (e.g., the motor threshold location) on the central sulcus 702, as illustrated in FIGS. 7A and 7B. The magnetic stimulation component 650 may or may not include a core, such as a magnetic core (e.g., ferromagnetic core), for example. The pulsing magnetic field 665 may include a test pulse (e.g., used during a MT detection procedure) and/or one or more pulse bursts (e.g., used during a treatment procedure). A pulse burst (e.g., each pulse burst) of the pulsing magnetic field 665 may include one or more pulses.

The sensor 610 may be configured to generate a signal associated with a pulsing magnetic field 665. The sensor 210 may be placed between the magnetic stimulation component 650 and a treatment area of a patient. The sensor 610 may be configured to generate a signal associated with the pulsing magnetic field 665 of the magnetic stimulation component 650 (e.g., a signal induced by the pulsing magnetic field 665). For example, the sensor 610 may convert a physical property (e.g., the strength of pulsing magnetic field 665) into a corresponding electrical signal (e.g., a current signal or a voltage signal). As such, the sensor 610 may detect and/or measure a physical parameter of the pulsing magnetic field and generate a signal associated with the pulsing magnetic field using the detected/measured physical parameter. The generated signal may be a voltage signal, a current signal, and/or the like that may be proportional to a change in the pulsing magnetic field 665. For example, a current may be generated in the sensor 610 that may be proportional to the pulsing magnetic field 665. The sensor 610 may generate a voltage that may be proportional to the magnetic flux density (dB/dt) of the pulsing magnetic field 665.

The sensor 610 may include one or more of a conductive coil, a loop (e.g., having a number of turns based on the pulsing magnetic field), a Hall sensor, a magnetoresistive material, a Faraday effect sensor, a Kerr effect sensor, a flux gate sensor, an inductance change element, a nerve tissue response measurement device, an electric field sensor (e.g., in a conductive field), and/or the like. The sensor 610 may be configured to generate more than one signal, for example, more than one signal that is associated with the pulsing magnetic field 665 generated by the magnetic stimulation component 650.

The controller 620 may be any type of hardware, software, or combination thereof. The controller 620 may be configured to control one or more of the components of the magnetic stimulation system 600, such as the sensor 610, the user interface device 630, the power supply 640, and/or the magnetic stimulation component 650, for example to conduct magnetic stimulation therapy. For example, the controller 620 may include a general purpose processor, a special purpose processor, a conventional processor, a digital signal processor (DSP), a plurality of microprocessors, one or more microprocessors in association with a DSP core, a microcontroller, any other type of integrated circuit (IC), a state machine, and/or the like.

The controller 620 may be coupled to a memory 670 and may be configured to send and receive information from the memory 670. The memory 670 may comprise a computer-readable storage media or machine-readable storage media that maintains computer-executable instructions for performing one or more as described herein. For example, the memory 670 may comprise computer-executable instructions or machine-readable instructions that include one or more portions of the procedures described herein. The controller 620 may access the instructions from memory for being executed to cause the processor 670 to operate as described herein. The memory 670 may comprise computer-executable instructions for executing configuration software. For example, the computer-executable instructions may be executed by the controller 620 to perform, in part and/or in its entirety, one or more procedures as described herein. Further, the memory 670 may have stored thereon one or more settings and/or control parameters associated with the magnetic stimulation system 600, a motor threshold detection device 690, and/or a user interface device 680.

The controller 620 may be configured to receive inputs from a user interface device 630 of the magnetic stimulation system 600 and/or from the sensor 610, and in response to the inputs, may be configured to conduct magnetic stimulation therapy accordingly. For example, the controller 620 may perform signal coding, data processing, power control, input/output processing, and/or any other functionality that enables the controller 620 to operate the magnetic stimulation component 650 for magnetic stimulation. The controller 620 may include a drive circuit (not shown) that generates a drive signal for driving (e.g., powering, such as pulsing) the magnetic simulation component 650. In some examples, the drive circuit may be separate from the controller 620 and electrically coupled to the magnetic stimulation component 650. The controller 620 may be configured to send signals to the user interface device 680 that indicate the timing of the pulses of the magnetic field (e.g., that indicate the timing and power of the drive signals used to generate the magnetic field).

Further, the controller 620 may be configured to alter the drive signal provided to the magnetic stimulation component 650 based on inputs received from the user interface device 630 and/or the sensor 610. The controller 620 may be configured to estimate (e.g., measure) characteristics associated with the signal generated by the sensor 610 (e.g., associated with one or more peaks of the signal). The controller 620 may estimate a subset of the pulses of the signal or may estimate the signal continuously. By estimating characteristics of the signal, the controller 620 may estimate a model of what is occurring in the brain of a patient in response to the pulsing magnetic field.

Further, the controller 620 may determine whether a failure has occurred based on one or more characteristics of the signal generated by the sensor 610. In the event a failure is determined to have occurred, the controller 620 may enter a failure mode. In the failure mode, the controller 620 may pause the magnetic stimulation procedure, shut down the magnetic stimulation component 650, alert a user of the magnetic stimulation system 600, and/or alter a current applied to the magnetic stimulation component 650. For example, when the controller 620 enters the failure mode, the controller 620 may adjust the frequency at which it estimates characteristics of the generated signal. For example, the controller 620 may check for failures more frequently after a first failure is detected. Further, the magnetic stimulation system 600 may include an indicator that may indicate to a user of the magnetic stimulation system 600 that a failure has occurred. For example, the indicator may be a light, a speaker, an icon displayed on the user interface 630, and/or the like. An example of a failure detection procedure(s) that may be performed by the controller 620 is described in U.S. Pat. No. 10,183,172, the entirety of which is incorporated by reference herein in its entirety.

The user interface device 630 may include any type of interface in which a user of the magnetic stimulation system 600 may initiate, adjust, and/or end the magnetic stimulation procedure. For example, the user interface device 630 may be a personal computer (PC), a keyboard, a mouse, a display device such as a touchscreen display device, a wireless device, and/or the like, that allows for an interface between the user and the magnetic stimulation system 600. The user interface device 630 may be an example of the display device 106 of the treatment system 100. Further, in some examples, the controller 620 may be configured to initiate or adjust any operational settings of the user interface device 680 and/or the motor threshold detection device 690.

The power supply 640 may be any type of power source that provides sufficient energy for the magnetic stimulation component 650 to generate the pulsing magnetic field 665 for its intended purpose, for example, for TMS, rTMS, MST or any other type of application. For example, the power supply 640 may be a conventional 120 or 240 VAC main power source.

The magnetic stimulation system 600 may be coupled to the user interface device 680. The user interface device 680 may be coupled to a motor threshold detection device 690. The motor threshold detection device 690 may be an example of the motor threshold detection device 200. The motor threshold detection device 690 may include a controller 692, one or more sensors 694, and memory 696.

The controller 692 may be any type of hardware, software, or combination thereof. The controller 692 may be configured to control one or more of the components of the motor threshold detection device 690. For example, the controller 692 may include a general purpose processor, a special purpose processor, a conventional processor, a digital signal processor (DSP), a plurality of microprocessors, one or more microprocessors in association with a DSP core, a microcontroller, any other type of integrated circuit (IC), a state machine, and/or the like.

The controller 692 may be coupled to a memory 696 and may be configured to send and receive information from the memory 696. The memory 696 may comprise a computer-readable storage media or machine-readable storage media that maintains computer-executable instructions for performing one or more as described herein. For example, the memory 696 may comprise computer-executable instructions or machine-readable instructions that include one or more portions of the procedures described herein. The controller 692 may access the instructions from memory for being executed to cause the controller 696 to operate as described herein. The memory 696 may comprise computer-executable instructions for executing configuration software. For example, the computer-executable instructions may be executed by the controller 692 to perform, in part and/or in their entirety, one or more procedures as described herein. Further, the memory 696 may have stored thereon one or more settings and/or control parameters associated with the motor threshold detection device 690.

The sensors 694 may be an example of the sensors 226a, 226b, and 226c. For example, the sensors 694 may comprise accelerometers or any other sensors capable of detecting motion of an object.

The controller 692 may be configured to detect the movement of one or more fingers (e.g., or other body parts) of a human subject, for example, through the use of one or more depressible members (e.g., the depressible members 202a, 202b, and 202c). In response to detecting the movement of a depressible member, the controller 692 may be configured to send one or more signals that indicate the timing and/or the amount of movement of the depressible member(s), for example, to the user interface device 680 and/or to the magnetic stimulation system 600. The controller 692 may be configured to detect the movement of the depressible members using the one or more sensors 664.

The user interface device 680 may be an example of the motor threshold device user interface 400. The user interface device 680 may include a controller 682, a display 684, and memory 686. The controller 682 may be any type of hardware, software, or combination thereof. The controller 682 may be configured to control one or more of the components of the user interface device 680. For example, the controller 682 may include a general purpose processor, a special purpose processor, a conventional processor, a digital signal processor (DSP), a plurality of microprocessors, one or more microprocessors in association with a DSP core, a microcontroller, any other type of integrated circuit (IC), a state machine, and/or the like.

The controller 682 may be coupled to a memory 686 and may be configured to send and receive information from the memory 686. The memory 686 may comprise a computer-readable storage media or machine-readable storage media that maintains computer-executable instructions for performing one or more as described herein. For example, the memory 686 may comprise computer-executable instructions or machine-readable instructions that include one or more portions of the procedures described herein. The controller 682 may access the instructions from memory for being executed to cause the processor 686 to operate as described herein. The memory 686 may comprise computer-executable instructions for executing configuration software. For example, the computer-executable instructions may be executed by the controller 682 to perform, in part and/or in their entirety, one or more procedures as described herein. Further, the memory 686 may have stored thereon one or more settings and/or control parameters associated with the user interface device 680.

The controller 682 may be configured to receive the signals from the motor threshold detection device 690 that indicate the timing and/or the amount of movement of one or more depressible members of the motor threshold detection device 690. The controller 682 may receive signals from the magnetic stimulation system 600 that indicate the timing and/or the power of the pulses of the magnetic field (e.g., that indicate the timing and power of the drive signals used to generate the magnetic field). As such, the controller 682 may be configured to determine whether the movement of a depressible member of the motor threshold detection device 690 occurred in response to a pulse of the magnetic field generated by the magnetic stimulation component 650 of the magnetic stimulation system 600 (e.g., or was a false positive).

The display device 684 may be an example of the display device 404 and/or the display device 520. The controller 682 may provide feedback to a user, such as a technician, during a procedure via the display device 684. For example, the controller 682 may be configured to generate an indication, via the display device 684, that indicates whether the movement of a depressible member of the motor threshold detection device occurred in response to a pulse of the magnetic field generated by the treatment coil of the treatment device (e.g., or was a false positive).

In some examples, the user interface device 680 may include a mounting clip (e.g., the mounting clip 406), such that the user interface device 680 may be mounted in fixed position for a user to view. In some examples, the user interface device 680 may be provided as part of the magnetic stimulation system 600, for example, as part of the user interface 630 of the magnetic stimulation system 600. Further, in some examples, the user interface device 680 may be part of the motor threshold detection device 690. Finally, it should be noted that in some examples, any combination of the magnetic stimulation system 600, the user interface device 680, and the motor threshold detection device 690 may be combined into a single device.

In some examples, the user interface device 680 may be integrated into a treatment system 600. In such instances, the output of the motor threshold detection device 690 may be received by the controller 620 of the treatment system 600, and the controller 620 may be configured to determine whether the movement of a depressible member of the motor threshold detection device 690 occurred in response to (e.g., coincides with) a pulse of the magnetic field generated by the magnetic stimulation component 650. Further, the controller 620 may be configured to provide feedback (e.g., via the user interface 630) to the technician that indicates the amount and/or the timing of an actuation of each, respective depressible member of a motor threshold detection device that occurred, and/or provide confirmation that the actuation of the depressible member resulted from a pulse of the magnetic field generated by the treatment device. In such instances, the user interface device 680 may be omitted because, for example, the functionality of the user interface device 680 may be performed by the treatment system 600.

Further, although described in context of the controller 682 and/or the controller 620, in some examples, an analog circuit (e.g., comprising a comparator) may be configured to receive output of the motor threshold detection device 690 and receive signals from the magnetic stimulation system 600 that indicate the timing and/or the power of the pulses of the magnetic field. The analog circuit may be configured to determine whether the movement of a depressible member of the motor threshold detection device 690 occurred in response to (e.g., coincides with) a pulse of the magnetic field generated by the magnetic stimulation component 650.

In some examples, the controller 620 of the treatment system 600 may receive the output signal of the motor threshold detection device 690 that indicates the amount and/or timing of the movement of a depressible member of the motor threshold detection device. The controller 620 may receive the signal in addition to or as an alternative to the user interface device 680 receiving the output signal of the motor threshold detection device. In such examples, the controller 620 may be configured to automatically adjust the level (e.g., power level) of a subsequent pulse of a magnetic field generated by the magnetic stimulation component 650 based on the output signal of the motor threshold detection device 690 that indicates the amount and/or timing of the movement of a depressible member of the motor threshold detection device (e.g., the feedback from the sensors 694). For example, if the output signal indicates that a depressible member associated with the thumb of the user moved, but only moved slightly, then the controller 620 may increase the power of a subsequent pulse of the magnetic stimulation component 650, for example, in an effort to increase the movement of the thumb of the patient (e.g., to exceed a threshold associated with a sufficient MT level for treatment, such as TMS).

Further, in some examples, the treatment system 600 may include a robotic arm that is configured to move the magnetic stimulation component 650 relative to the patient (e.g., relative to the patient's head). For instance, the controller 620 may be configured to control the movement of the magnetic stimulation component 650 prior to, or during, a MT processor or the treatment procedure itself. The controller 620 may be configured to automatically adjust the position of the magnetic stimulation component 650 prior to the generation of a subsequent pulse of the magnetic field based on the output signal of the motor threshold detection device 690 that indicates the amount and/or timing of the movement of a depressible member of the motor threshold detection device that occurred in response to a prior pulse of a magnetic field. For example, if the output signal indicates that the patient's middle and/or ring finger moved in response to a prior magnetic pulse, the controller 620 may be configured to cause the robotic arm to move the magnetic stimulation component 650 in a direction closer to the patient's MT location and pulse the coil again, for example, with the hopes that the subsequent pulse cases the patient's thumb to twitch. As such, using the feedback from the sensors 692 of the motor threshold detection device 690 and a robotic arm, the controller 620 may be configured to automatically adjust the position of the magnetic stimulation component 650 and search for the user's MT location using the output signal(s) received from the motor threshold detection device 690, for example, without requiring the technician to physically move the magnetic stimulation component 650 relative to the patient's head.

Further, in some examples, the controller 620 may be configured to automatically adjust both the position of the magnetic stimulation component 650 using the robotic arm and the power level of the pulses of the magnetic field to automate the MT location and MT stimulation level process. For example, the controller 620 may be configured to automatically adjust the position of the magnetic stimulation component 650 using the robotic arm between magnetic pulses of the magnetic stimulation component 650 to auto-matically determine the MT location. The controller 620 may also automatically adjust the stimulation level of the magnetic stimulation component 650 between magnetic pulses to automatically determine the MT stimulation level for the patient. Further, in such examples, the controller 620 may request and/or receive a confirmation from the techni-cian (e.g., via the user interface 630) once the MT location and the MT stimulation level are identified.

In some examples, the controller 682 and/or the controller 620 may be configured to determine whether the movement of a depressible member of the motor threshold detection device 690 occurred in response to (e.g., coincides with) a pulse of the magnetic field generated by the magnetic stimulation component 650 even in situations where the patient suffers from tremors. For instance, the controller 682 and/or the controller 620 may be configured to measure the periodic motion that occurs as a result of the tremor before the magnetic pulse is generated, and subtract tremor motion from the resulting motion that is detected by the sensors 694 during the magnetic pulse (e.g., during the time window), for example, to determine the amount and/or the timing of any movement that occurred as a results of pulse of the magnetic field generated by the magnetic stimulation com-ponent 650.

Figure 8:
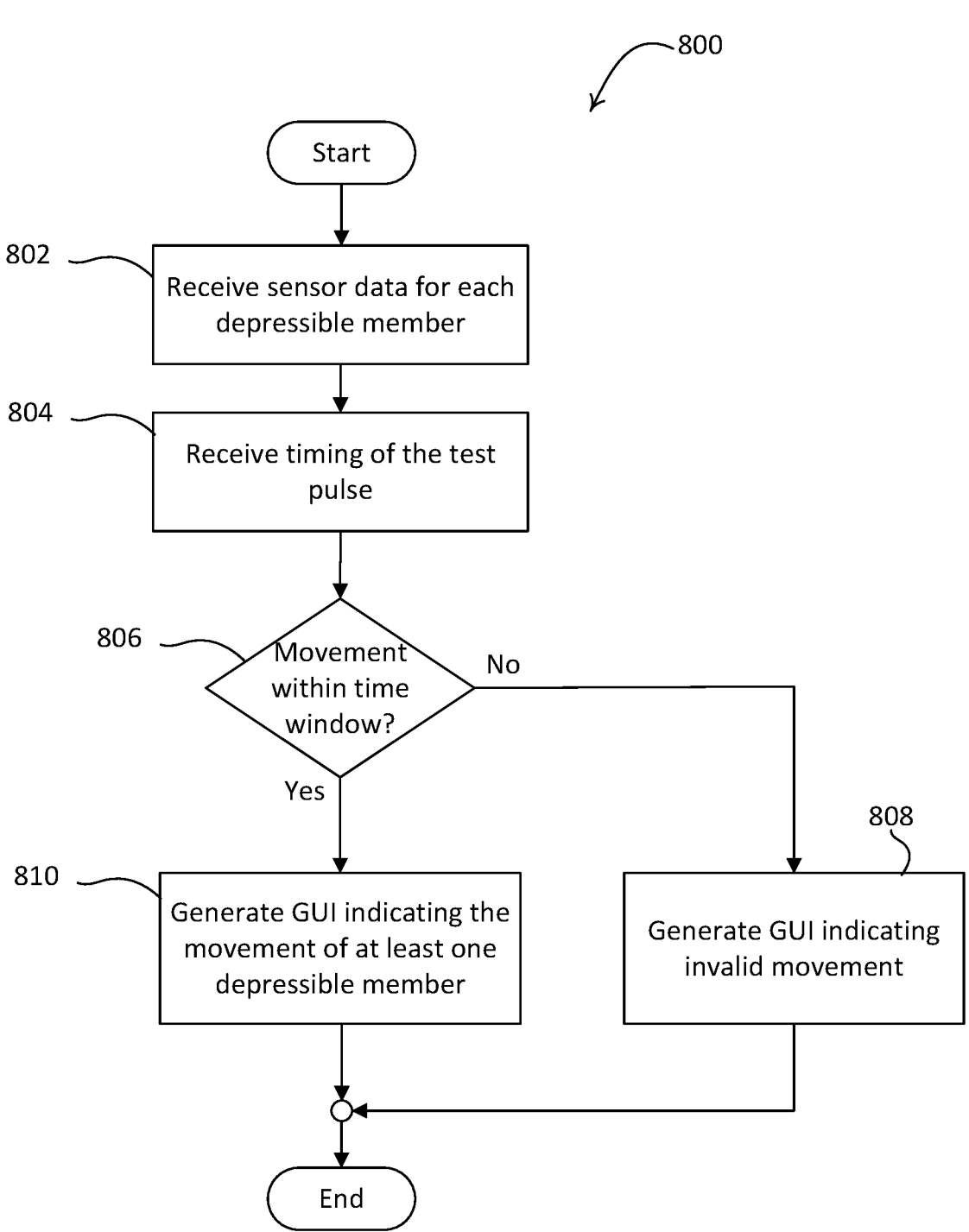
FIG. 8 is a flow diagram of an example TMS procedure.

FIG. 8 is a flowchart of an example procedure 800 for determining movement of one or more depressible members and generating a graphical UI (GUI) accordingly. The pro-cedure 800 may be performed by a controller of a treatment system, such as the processor of the treatment system 100, the controller of the motor threshold detection device 200, the controller of the user interface device 400, the controller 620 of the magnetic stimulation system 600, the controller 682 of the user interface device 680, and/or the controller 692 of the motor threshold detection device 690. The controller may perform the procedure 800 to detect move-ment of one or more depressible members and determine whether the movement of a depressible member occurred in response to a pulse of a magnetic field. Further, the control-ler may generate a GUI via a display device (e.g., the display device 106, the display device 404, the display device 520, the user interface 630, and/or the display device 684) that indicates whether or not the movement of a depressible member occurred in response to a pulse of a magnetic field to, for example, assist a technician in determining a MT position on the human subject.

The controller may perform the procedure 800 in response to a magnetic stimulation device (e.g., the treatment coil 102 or the magnetic stimulation component 650) generating a test pulse to determine the motor threshold position on the human subject. Alternatively or additionally, the controller may perform the procedure 800 periodically.

Prior to the procedure beginning, a human subject may position his or her fingers on the respective depressible members of a motor threshold detection device (e.g., the motor threshold detection device 200). A technician may position the magnetic stimulation device on, for example, the head of the human subject. In some examples, to begin the procedure, the technician may generate one or more test pulses (i.e., magnetic pulses) using the treatment system.

At 802, the controller may receive signals from the motor threshold detection device for each depressible member. For example, the controller may receive sensor data (e.g., data from one or more of sensors 226a, 226b, 226c) that indicate the timing and/or the amount of movement for one or more depressible members of the motor threshold detection device (e.g., the depressible members 202a, 202b, and 202c). As described herein, the motor threshold detection device may be configured to generate signals that indicate the timing and/or the amount of movement of one or more depressible members, and send those signals to the controller.

At 804, the controller may be configured to receive a signal that indicates the timing and/or the power level of a test pulse (e.g., a timing pulse or a sync pulse) at 804. For example, the treatment system may generate one or more test pulses during a motor threshold detection procedure. The treatment system may send the signals indicating the timing of the test pulses to the controller.

At 806, the controller may be configured to determine whether the movement of one or more depressible members occurred within a time window around the test pulse. For example, the controller may be configured to compare the timing of the signals received from the motor threshold detection device (at 802) with the timing of the signals received from the magnetic stimulation device (at 804) to determine whether the signals received from the motor threshold detection device occurred at substantially the same time as (e.g., with the time window) the signals received from the magnetic stimulation device. As such, the control-ler may be configured to determine whether the movement of a depressible member of the motor threshold detection device occurred in response to a pulse of the magnetic field generated by the treatment coil of the treatment device, or whether the movement of a depressible member occurred in response to an unrelated movement of the human subject (e.g., a movement unrelated to the magnetic stimulation device). In some examples, the time window may be con-figured to be short enough to account for the time it takes for the controller to receive the signals from the motor threshold detection device and the magnetic stimulation device. For instance, in some examples the time window may be approximately 0.25 seconds after the magnetic pulse was generated. In other examples, the time window may be set such that it is between 20 ms to 250 ms after the magnetic pulse was generated. Some patients may react to the sound of the magnetic pulse being generated by the treatment system, while others may anticipate the pulse and react quickly. The system should be designed to avoid these false positive movements.

If the controller determines that the movement of one or more depressible members did not occur within the time window around the test pulse at 806, the controller may ignore the movement and/or determine that the movement was not a valid movement that occurred in response to the magnetic pulse. For example, the controller may generate a GUI via the display device that indicates that the movement of the depressible member(s) was an invalid movement at 808. Therefore, in such examples, the technician may receive confirmation that the movement of the depressible member did not occur in response to a pulse of the magnetic field generated by the magnetic stimulation device (e.g., the movement was a false positive). As such, the technician would know that the coil is not located at the human subject's MT location, and in response, may move the placement of the treatment coil and/or changes the strength of the magnetic pulse, and then generates another test pulse.

Further, it should be appreciated that in some examples, if the controller determines that the movement of one or more depressible members did not occur within a time window around the test pulse at 806, the controller may not generate a GUI and the procedure 800 may end. Further, in some examples, if the controller determines that the move-ment of one or more depressible members did not occur within a time window around the test pulse at 806, the controller may be configured to detect (e.g., diagnose) nerve damage and/or a neurodegenerative disease in the patient. For example, the controller may determine that the patient is at risk of having Amyotrophic lateral sclerosis (ALS) based on a delay between the magnetic pulse and the time of the movement of the depressible members (e.g., a small amplitude, delayed and desynchronized primary peaks of the magnetic field, along with longer excitatory postsynaptic potential (EPSP) rise times of reduced amplitude).

If the controller determines that the movement of one or more depressible members occurred within the time window around the test pulse at 806, the controller may generate a GUI via the display device that indicates the movement of the at least one depressible member (e.g., via indicia) at 810. For instance, if the magnetic pulse was generated at time t=0, the time window may be configured such that the controller will ignore the movement if it occurs within a first time range (e.g., 20 ms) after the generation of the magnetic pulse (e.g., between t=0 up to t=20 ms), may detect a valid movement if the movement occurs within a time window between from the first time range to a second time range (e.g., between 20 ms to 250 ms) after the generation of the magnetic pulse, and ignore the movement if it occurs more than the second time range (e.g., 250 ms) after the generation of the magnetic pulse.

The controller may generate a GUI via the display device that indicates that the movement of the depressible member(s) was caused by a pulse of a magnetic field generated by the magnetic stimulation device at 810. Alternatively or additionally, the controller may generate a GUI via the display device that indicates that the magnetic stimulation device is located at the patient's MT location. In some examples, the controller may generate a GUI via the display device that indicates a direction that the magnetic stimulation device should be moved so that the magnetic stimulation device is located at the human subject's MT location and/or treatment location. Further, in some instances, the controller may generate a GUI via the display device that indicates, via indicia, which depressible member(s) was moved and/or an amount of movement of the depressible member(s). Examples of GUIs that may be generated by the controller at 810 may be those depicted in FIGS. 5A-5C, although the procedure 800 is not limited to just these GUIs.

Accordingly, using the procedure 800, the technician may be assisted in locating the proper position for the magnetic stimulation device for treatment of the human subject. For instance, using the procedure 800, the technician may be assisted in locating the user's MT location and/or treatment location. If the controller detects an invalid movement at 806 and 808, then the technician may repeat procedure 800 until the technician positions the magnetic stimulation device at the MT location. Finally, as noted herein, in some examples the MT location may be the location that causes a specific response by the human subject, such as an involuntary twitch of the human subject's thumb. After the MT location is detected, the technician may use the MT location to determine the treatment location. For example, in the case of using the TMS coil for treatment of depression, the treatment location may be determined by moving the magnetic stimulation device from the MT location along a line in the anterior direction a prescribed distance (e.g., a distance is 5 cm) to identify the treatment location on the subject.

Finally, although described in context of a GUI, in some instances, the controller may generate a notification via another user interface at 808 and/or at 810 (e.g., in addition to or as an alternative to the generation of a GUI). For example, the controller may generate an audible notification via a speaker of the system (e.g., the treatment system may comprise a speaker). Alternatively or additionally, the controller may illuminate one or more light sources (e.g., light-emitting diodes) that indicate whether a depressible member moved in response to a pulse of the magnetic field. In some examples, the motor threshold detection device may include the light source(s). For instance, a light source may be located adjacent to or in proximity to each depressible member (e.g., the light source may be located on or integrated into the depressible member), and the controller may illuminate the light sources to indicate whether the depressible member moved in response to a pulse of the magnetic field (e.g., green or on if the depressible member moved in response to the pulse of the magnetic field, and red or off if the depressible member did not move in response to a pulse of the magnetic field).

One of ordinary skill in the art will appreciate that these and other different configurations of the example TMS devices may be implemented without departing from the scope and spirit of the instant disclosure.

What is claimed is:

1. A system for detecting movement of a human subject when determining a position of a motor threshold or a treatment location of the human subject during a treatment or procedure, the system comprising:
   a plurality of depressible members, wherein each depressible member is configured to move in response to movement of a finger of the human subject;
   a plurality of sensors, wherein each depressible member is associated with at least one sensor, and wherein each sensor is configured to sense movement of at least one of the plurality of depressible members; and
   a processor configured to:
      receive a feedback signal from each of the plurality of sensors;
      receive a signal that indicates a generation time of a magnetic stimulation pulse;
      determine that the feedback signal from at least one of the plurality of sensors indicates movement above a threshold within a time window after the generation time of the magnetic stimulation pulse; and
      generate, via a user interface, a notification that indicates that at least one of the plurality of depressible members moved in response to the magnetic stimulation pulse.

2. The system of claim 1, wherein the notification indicates an amount of movement of the at least one depressible member that moved in response to the magnetic stimulation pulse.

3. The system of claim 2, wherein the notification comprises a meter to indicate the amount of movement of the at least one depressible member that moved in response to the magnetic stimulation pulse.

4. The system of claim 3, wherein the meter comprises first indicia that indicates the amount of movement of the depressible member during a present magnetic stimulation pulse, and second indicia that indicates the amount of movement of the depressible member during a previously generated magnetic stimulation pulse.

5. The system of claim 1, wherein the plurality of depressible members comprises a first depressible member that is configured to receive a thumb of the human subject, wherein movement of the first depressible member indicates that a stimulation coil that generated the magnetic stimulation pulse is located at the motor threshold location of the human subject.

6. The system of claim 5, wherein the plurality of depressible members further comprises a second depressible member that is configured to receive an index finger and a middle finger of the human subject, and a third depressible member that is configured to receive a ring finger and a pinky finger of the human subject.

7. The system of claim 1, wherein the plurality of sensors comprise a plurality of accelerometers.

8. The system of claim 1, further comprising:
a base configured to receive the subject's palm, wherein the base is rigidly fixed and configured to remain steady during movement by the fingers of the human subject.

9. The system of claim 1, further comprising:
a plurality of spring arms, wherein each of the depressible members is associated with at least one spring arm, and wherein the spring arm is configured to allow the depressible member to move in response to movement of the finger of the human subject.

10. The system of claim 1, further comprising:
a user interface device, wherein the user interface device comprises the user interface.

11. The system of claim 10, wherein the user interface comprises a display device.

12. The system of claim 1, further comprising:
an electromagnet;
a drive circuit electrically coupled to the electromagnet; and
a second processor configured to control the drive circuit to provide current to the electromagnet to generate the magnetic stimulation pulse.

13. The system of claim 12, wherein the second processor is further configured to provide the signal that indicates the generation time of the magnetic stimulation pulse to the processor.

14. A system for detecting movement of one or more bodies of a human subject, the movement being generated in response to a magnetic stimulation pulse, the system comprising:
a motion detection device comprising:
a plurality of depressible members operably coupled to a base member, wherein the plurality of depressible members is configured to move about the base member in response to a movement of a respective body of the human subject; and
a plurality of sensors, wherein each sensor is coupled to a respective depressible member of the plurality of depressible members, and wherein each sensor is configured to detect movement of the respective depressible member; and
a processor configured to:
receive sensor data associated with detected movement of one or more of the plurality of depressible members;
receive a signal that indicates a generation time of the magnetic stimulation pulse;
determine that the sensor data indicates movement of the one or more plurality of depressible members within a time window associated with the generation time of the magnetic stimulation pulse; and
generate a notification indicating that at least one of the depressible members moved in response to the magnetic stimulation pulse.

15. The system of claim 13, wherein the processor is comprised within the motion detection device.

16. The system of claim 13, wherein the processor is comprised with a treatment device that comprises a stimulation coil that is configured to generate the magnetic stimulation pulse.

17. The system of claim 13, wherein the processor is comprised within a user interface device that comprises a display device, wherein the processor is configured to generate the notification via the display device.

18. The system of claim 13, wherein the notification indicates an amount of movement of the at least one depressible member that moved in response to the magnetic stimulation pulse.

19. The system of claim 13, wherein the plurality of depressible members comprises a first depressible member that is configured to receive a thumb of the human subject, wherein movement of the first depressible member indicates that a stimulation coil that generated the magnetic stimulation pulse is located at the motor threshold location of the human subject.

20. The system of claim 19, wherein the plurality of depressible members further comprises a second depressible member that is configured to receive an index finger and a middle finger of the human subject, and a third depressible member that is configured to receive a ring finger and a pinky finger of the human subject.

* * * * *